United States Patent
Elisseeff et al.

(10) Patent No.: US 10,227,369 B2
(45) Date of Patent: Mar. 12, 2019

(54) SHORT-CHAIN FATTY ACID HEXOSAMINE ANALOGS AND THEIR USE IN TISSUE ENGINEERING APPLICATIONS

(71) Applicant: THE JOHNS HOPKINS UNIVERSITY, Baltimore, MD (US)

(72) Inventors: Jennifer H. Elisseeff, Baltimore, MD (US); Kevin Yarema, Woodstock, MD (US); Jeannine Coburn, Baltimore, MD (US); Udayanath Aich, Brighton, MA (US)

(73) Assignee: The Johns Hopkins University, Baltimore, MD (US)

( * ) Notice: Subject to any disclaimer, the term of this patent is extended or adjusted under 35 U.S.C. 154(b) by 317 days.

(21) Appl. No.: 14/774,805

(22) PCT Filed: Mar. 11, 2014

(86) PCT No.: PCT/US2014/023316
§ 371 (c)(1),
(2) Date: Sep. 11, 2015

(87) PCT Pub. No.: WO2014/164723
PCT Pub. Date: Oct. 9, 2014

(65) Prior Publication Data
US 2016/0016985 A1    Jan. 21, 2016

Related U.S. Application Data

(60) Provisional application No. 61/777,405, filed on Mar. 12, 2013.

(51) Int. Cl.
| | |
|---|---|
| *C07H 13/04* | (2006.01) |
| *A61K 31/7008* | (2006.01) |
| *A61K 45/06* | (2006.01) |
| *A61K 31/7024* | (2006.01) |

(52) U.S. Cl.
CPC ......... *C07H 13/04* (2013.01); *A61K 31/7008* (2013.01); *A61K 31/7024* (2013.01); *A61K 45/06* (2013.01)

(58) Field of Classification Search
None
See application file for complete search history.

(56) References Cited

U.S. PATENT DOCUMENTS

| 5,589,466 A | 12/1996 | Felgner et al. |
|---|---|---|
| 2006/0083778 A1 | 4/2006 | Allison et al. |
| 2010/0137241 A1 | 6/2010 | Elisseeff et al. |

FOREIGN PATENT DOCUMENTS

WO    1994-28889 A1    12/1994

OTHER PUBLICATIONS

Almaraz et al., Biotechnology and Bioengineering, 2012, 109(4), pp. 992-1006.*
Matsumura et al., Organic Letters, 2008, vol. 10(8), 1557-1560.*
Ljevakovic et al., AN 1989:213238—Carbohydrate Research, 1988, 182(2), 197-205.*
Almaraz, R., et al., "Metabolic oligosaccharide engineering with N-Acyl functionalized ManNAc analogs: cytotoxicity, metabolic flux, and glycan-display considerations", Biotechnol. Bioeng., Nov. 8, 2011, vol. 109, No. 4, pp. 992-1006.
Mathew, M., et al., "Extracellular and intracellular esterase processing of SCFA-hexosamine analogs: implications for metabolic glyco-engineering and drug delivery", Bioorg. Med. Chem. Lett., Sep. 13, 2012, vol. 22, No. 222, pp. 6929-6933.
Coburn, J., et al., "Short-chain fatty acid-modified hexosamine for tissue-engineering osteoarthritic cartilage", Tissue Eng. Part A, Jun. 8, 2013, vol. 19, No. 17-18, pp. 2035-2044.
Campbell, C., et al., "Targeting pro-invasive oncogenes with short chain fatty acid-hexosamine analogues inhibits the mobility of metastatic MDS-MB-231 breast cancer cells", J. Med. Chem. (2008) vol. 51, No. 24, pp. 8135-8147.
Mengshol, J., et al., "IL-1 induces collagenase-3 (MMP-13) promoter activity in stably transfected chondrocytic cells: requirement for Runx-2 and activation by p38 MAPK and JNK pathways", Nucleic Acids Research, (2001) vol. 20, No. 21, pp. 4361-4372.
Aich, et al., Regioisomeric SCFA attachment to hexosamines separates metabolic flux from cytotoxicity and MUC1 suppression. ACS Chem Biol. Apr. 18, 2008;3(4):230-40.
Martens, et al., Characterization of hydrogels formed from acrylate modified poly(vinyl alcohol) macromers. Polymer. Oct. 2000;41(21):7715-7722.
Elmouelhi, et al., The Hexosamine Template—A Platform for Modulating Gene Expression and for Sugar-based Drug Discovery. J Med Chem. Apr. 23, 2009; 52(8): 2515-2530.
Varghese, et al., Chondroitin sulfate based niches for chondrogenic differentiation of mesenchymal stem cells. Matrix Biol. Jan. 2008;27(1):12-21.

(Continued)

*Primary Examiner* — Traviss C McIntosh, III
(74) *Attorney, Agent, or Firm* — Johns Hopkins Tech Ventures

(57) ABSTRACT

A new class of molecules, $C_1$—OH tributanoylated hexosamines, including, for example, GalNAc, GlcNAc and ManNAc, are demonstrated to increase cartilage-like tissue accumulation by IL-1β-stimulated chondrocytes. Furthermore, all three molecules reduced NFKB1 and IκBα driven gene expression, consistent with NFκB inhibitory properties of these analogs. GalNAc-a exposure produced the greatest ECM accumulation by IL-1β-stimulated chondrocytes. However, GalNAc-a exposure produced an opposite effect on MSC exposure, where a decrease in ECM accumulation was observed. These findings are in support of the function of NFκB signaling during limb development and growth plate chondrogenesis. The present invention shows the capability of this new class of hexosamine analogs as disease-modifying agents for treating cartilage damage.

12 Claims, 18 Drawing Sheets
Specification includes a Sequence Listing.

(56) References Cited

OTHER PUBLICATIONS

Sun, et al., NF-kappa B controls expression of inhibitor I kappa B alpha: evidence for an inducible autoregulatory pathway. Science. Mar. 26, 1993;259(5103):1912-5.
Lawrence, et al., Estimates of the prevalence of arthritis and other rheumatic conditions in the United States. Part II. Arthritis Rheum. Jan. 2008;58(1):26-35.
Li, et al., Matrix metalloproteinases and inhibitors in cartilage tissue engineering. J Tissue Eng Regen Med. Feb. 2012;6(2):144-54.
Otsuki, et al., The effect of glycosaminoglycan loss on chondrocyte viability: a study on porcine cartilage explants. Arthritis Rheum. Apr. 2008;58(4):1076-85.
Hedbom, et al., Molecular aspects of pathogenesis in osteoarthritis: the role of inflammation. Cell Mol Life Sci. Jan. 2002;59(1):45-53.
Benito, et al., Synovial tissue inflammation in early and late osteoarthritis. Ann Rheum Dis. Sep. 2005;64(9):1263-7.
Pahl, Activators and target genes of Rel/NF-kappaB transcription factors. Oncogene. Nov. 22, 1999;18(49):6853-66.
Moos, et al., Immunohistological analysis of cytokine expression in human osteoarthritic and healthy cartilage. J Rheumatol. Apr. 1999;26(4):870-9.
Meutermans, et al., Carbohydrates as scaffolds in drug discovery. ChemMedChem. Nov. 2006;1(11):1164-94.
Shikhman, et al., N-acetylglucosamine prevents IL-1 beta-mediated activation of human chondrocytes. J Immunol. Apr. 15, 2001;166(8):5155-60.
Hwang, et al., N-Acetylglucosamine suppress collagenases activation in ultraviolet B-irradiated human dermal fibroblasts: Involvement of calcium ions and mitogen-activated protein kinases. J Dermatol Sci. Aug. 2011;63(2):93-103.
Shikhman, et al., Chondroprotective activity of N-acetylglucosamine in rabbits with experimental osteoarthritis. Ann Rheum Dis. Jan. 2005; 64(1): 89-94.
Sun, et al., A 3D cartilage—inflammatory cell culture system for the modeling of human osteoarthritis. Biomaterials. Aug. 2011;32(24):5581-9.
Kim, et al., Experimental model for cartilage tissue engineering to regenerate the zonal organization of articular cartilage. Osteoarthritis Cartilage. Sep. 2003;11(9):653-64.
Kim, et al., Fluorometric assay of DNA in cartilage explants using Hoechst 33258. Anal Biochem. Oct. 1988;174(1):168-76.
Farndale, et al., Improved quantitation and discrimination of sulphated glycosaminoglycans by use of dimethylmethylene blue. Biochim Biophys Acta. Sep. 4, 1986;883(2):173-7.
Woessner, The determination of hydroxyproline in tissue and protein samples containing small proportions of this imino acid. Arch Biochem Biophys. May 1961;93:440-7.
Livak et al. Analysis of relative gene expression data using real-time quantitative PCR and the 2(-Delta Delta C(T)) Method. Methods. Dec. 2001;25(4):402-8.
Stokes, et al., Assessment of the gene expression profile of differentiated and dedifferentiated human fetal chondrocytes by microarray analysis. Arthritis Rheum. Feb. 2002;46(2):404-19.
Sharma, et al., Designing zonal organization into tissue-engineered cartilage. Tissue Eng. Feb. 2007;13(2):405-14.
Bryant, et al., Hydrogel properties influence ECM production by chondrocytes photoencapsulated in poly(ethylene glycol) hydrogels. J Biomed Mater Res. Jan. 2002;59(1):63-72.
Lee, et al., Novel poly(ethylene glycol) scaffolds crosslinked by hydrolyzable polyrotaxane for cartilage tissue engineering. J Biomed Mater Res A. Dec. 15, 2003;67(4):1087-92.
Lin-Gibson, et al., Synthesis and characterization of PEG dimethacrylates and their hydrogels. Biomacromolecules. Jul.-Aug. 2004;5(4):1280-7.
Elisseeff, et al., Photoencapsulation of chondrocytes in poly(ethylene oxide)-based semi-interpenetrating networks. J Biomed Mater Res. Aug. 2000;51(2):164-71.
Sims, et al., Injectable cartilage using polyethylene oxide polymer substrates. Plast Reconstr Surg. Oct. 1996;98(5):843-50.
Zhang, et al., A potent small molecule inhibits polyglutamine aggregation in Huntington's disease neurons and suppresses neurodegeneration in vivo. Proc Natl Acad Sci U S A. Jan. 18, 2005;102(3):892-7.
Friman, et al., Sotrastaurin, a Novel Small Molecule Inhibiting Protein-Kinase C: Randomized Phase II Study in Renal Transplant Recipients. Am J Transplant. 2011;11:1444-1455.
MacMillan, et al., Development of proneurogenic, neuroprotective small molecules. J Am Chem Soc. Feb. 9, 2011;133(5):1428-37.
Hong, et al., Applications of small molecule BMP inhibitors in physiology and disease. Cytokine Growth Factor Rev. Oct.-Dec. 2009;20(5-6):409-18.
Milne, et al., Small molecule activators of SIRT1 as therapeutics for the treatment of type 2 diabetes. Nature. Nov. 29, 2007;450(7170):712-6.
Calamini, et al., Small-molecule proteostasis regulators for protein conformational diseases. Nat Chem Biol. Dec. 25, 2011;8(2):185-96.
Mow, et al., Cartilage and diarthrodial joints as paradigms for hierarchical materials and structures. Biomaterials. 1992;13(2):67-97.
Chabane, et al., Histone deacetylase inhibitors suppress interleukin-1beta-induced nitric oxide and prostaglandin E2 production in human chondrocytes. Osteoarthritis Cartilage. Oct. 2008;16(10):1267-74.

* cited by examiner

SHORT-CHAIN FATTY ACID HEXOSAMINE ANALOGS AND THEIR USE IN TISSUE ENGINEERING APPLICATIONS

REFERENCE TO RELATED APPLICATIONS

This application claims the benefit of U.S. Provisional Patent Application No. 61/777,405, filed on Mar. 12, 2013, which is hereby incorporated by reference for all purposes as if fully set forth herein.

STATEMENT OF GOVERNMENTAL INTEREST

This invention was made with government support under grant no. AR054005, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 7, 2014, is named P11014-04_ST25.txt and is 6,177 bytes in size.

BACKGROUND OF THE INVENTION

Articular cartilage covers the surfaces of all diarthroidal joints. It is a highly hydrated tissue that serves to distribute loads to bone ends and facilitates near frictionless movement. Damage to articular cartilage via trauma or disease is a clinical challenge, as the tissue has limited ability to self-repair, leaving it vulnerable to further degeneration. There are two cell types commonly investigated in the repair of cartilage: chondrocytes and mesenchymal stem cells (MSCs). Chondrocytes are the resident cells in articular cartilage. They produce the extracellular matrix (ECM) and release degradation enzymes to remove aging matrix, maintaining tissue homeostasis. MSCs are multipotent stem cells with the ability to differentiate into multiple cell lineages, including chondrocytes, and reside within the bone marrow. A common surgical strategy used to repair articular cartilage defects, microfracture, utilizes MSCs naturally residing within the bone marrow as a cell source for tissue repair.

Damage to diarthroidal joint tissue, whether due to sports injuries or overuse, causes early-onset osteoarthritis (OA) through multiple mechanisms, including joint instability that causes irregular force distribution and local inflammation. To date, there are no disease-modifying drugs for effective management or treatment of OA. Preventative therapeutics that reduce the progressive cartilage damage after injury could potentially decrease the prevalence of early-onset OA. Local inflammation is a potential therapeutic target, as inflammation results in increased levels of ECM degradation enzymes. Inflammation can be driven by inflammatory cytokines or other stimuli. The inflammatory process triggers increased expression of pro-inflammatory cytokines creating a positive feedback loop and further perturbs joint space homeostasis. The Nuclear factor-κB (NFκB) signaling pathway is a mechanism that controls the transcription of inflammatory cytokines and degradation enzymes implicated in OA. As NFκB is a significant factor in the inflammatory process, inhibition of NFκB activity has been proposed as a potential therapeutic target.

Current available OA therapeutics target pain management and increased mobility at later stages of tissue damage. There remains a significant need to develop disease-modifying agents that reduce OA progression and restore cartilage homeostasis. Patients who may benefit the most from disease-modifying approaches are those with sports-related or overuse injuries which are strong predictors for OA later in life and those undergoing knee surgery. After injury or surgery there is an increase in inflammatory molecules within the joint space that are purported instigators of OA development.

Therefore, there exists a significant need to develop therapeutic strategies to increase the regenerative capacity of cells that could repair cartilage.

SUMMARY OF THE INVENTION

In accordance with one or more embodiments, the inventors provide a platform technology containing multiple N-acetylhexosamines functionalized in a similar manner, specifically 3,4,6-O-Bu$_3$GlcNAc, 3,4,6-O-Bu$_3$GalNAc, and 3,4,6-O-Bu$_3$ManNAc. The chemical structures of ,4,6-O-Bu$_3$GlcNAc, 3,4,6-O-Bu$_3$GalNAc, and 3,4,6-O-Bu$_3$ManNAc are shown in FIGS. 1A-C. These molecules are subsequently denoted as GlcNAc-a, GalNAc-a, and ManNAc-a, respectively, in this application. The general effects of these analogs were evaluated on IL-1β-stimulated chondrocytes and on chondrogenic-induced MSCs to determine their potential to be developed into disease-modifying agents for treating cartilage damage. The present invention therefore provides a class of hexosamine analogs as disease modifying agents for treating cartilage damage and for developing cartilage therapeutics.

In accordance with an embodiment, the present invention provides a compound of formula I:

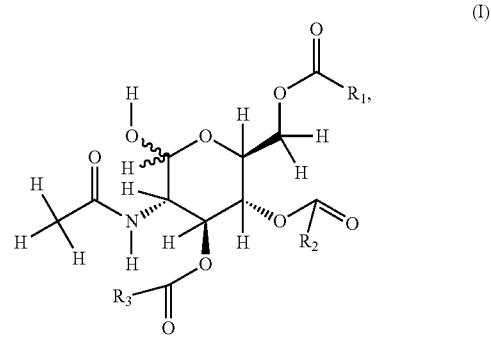

a compound of formula II:

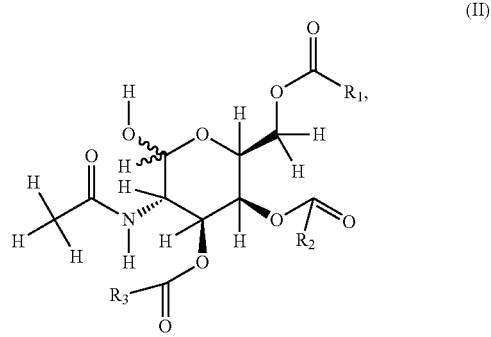

a compound of formula III:

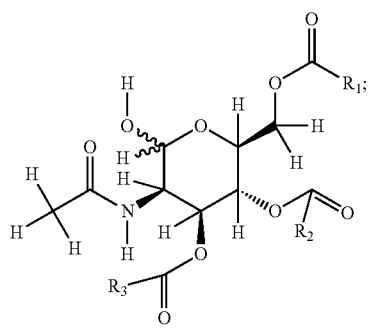

(III)

wherein $R_1$, $R_2$, and $R_3$ are the same or different, and are $C_1$-$C_6$ alkyl substituents.

In accordance with another embodiment, the present invention provides the compounds of formulas I-III, wherein $R_1$, $R_2$, and $R_3$ of the compounds of formulas I-III are $C_3$ alkyl groups and are selected from group consisting of:

(compound 1)

(compound 2)

, and (compound 3)

.

In accordance with an embodiment, the present invention provides a method for treating joint disease in a mammal comprising: a) administering to the cartilage in need of treatment a composition comprising a compound of formula I:

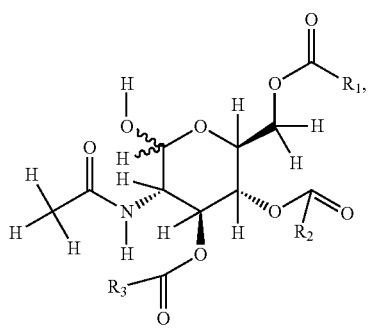

(I)

a compound of formula II:

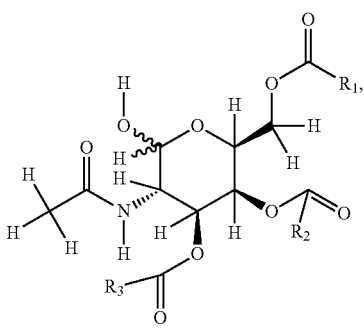

(II)

a compound of formula III:

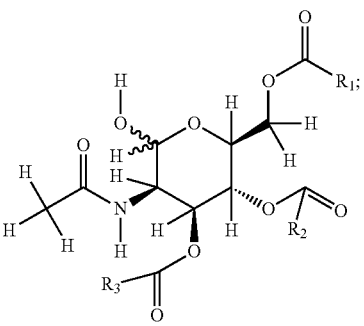

(III)

wherein $R_1$, $R_2$, and $R_3$ are the same or different, and are $C_1$-$C_6$ alkyl substituents.

In accordance with another embodiment, the present invention provides a method for treating joint disease in a mammal comprising: a) administering to the cartilage in need of treatment a composition comprising the compounds of formulas I-III, wherein $R_1$, $R_2$, and $R_3$ of the compounds of formulas I-III are $C_3$ alkyl groups and are selected from group consisting of:

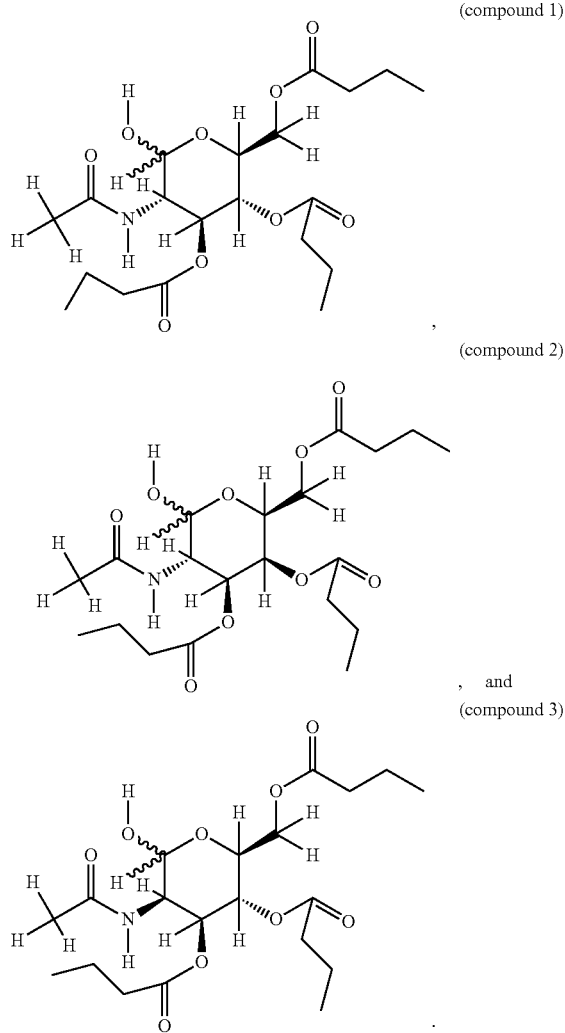

(compound 1), (compound 2), and (compound 3)

In accordance with a further embodiment, the present invention provides a method for treating joint disease in a mammal comprising any of the compositions described above in a biocompatible hydrogel.

In accordance with yet another embodiment, the present invention provides a method for treating joint disease in a mammal comprising any of the compositions described above in a biocompatible hydrogel and at least one additional biologically active agent.

DETAILED DESCRIPTION OF THE INVENTION

Figure 1:
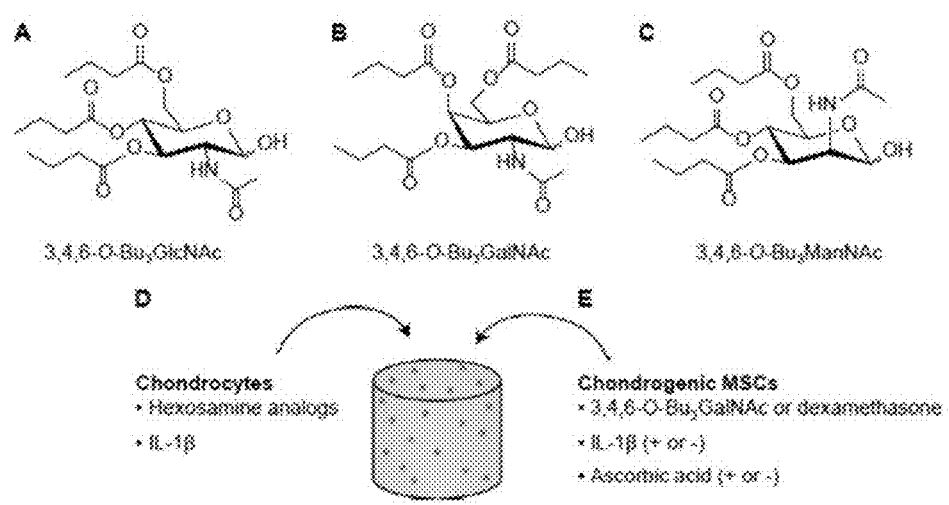
FIG. 1 depicts the outline of experimental design. Chemical structures of $C_1$—OH tributanoylated hexosamines, including specific examples, (A) N-acetylglucosamine (GlcNAc-a), (B) N-acetylgalactosamine (GalNAc-a) and (C) N-acetylmanosamine (ManNAc-a). (D) Chondrocytes and (E) chondrogenic-induced MSCs were cultured in 3D poly (ethylene glycol)-diacrylate (PEGDA) hydrogels. (D) IL-1β-stimulated chondrocytes were exposed to varying concentrations of each of the three analogs in separate experiments. (E) Chondrogenic-induced MSCs were cultured with or without IL-1β in combination with varying concentrations of GalNAc-a or 100 nM dexamethasone.

In accordance with an embodiment, the present invention provides a compound of formula I:

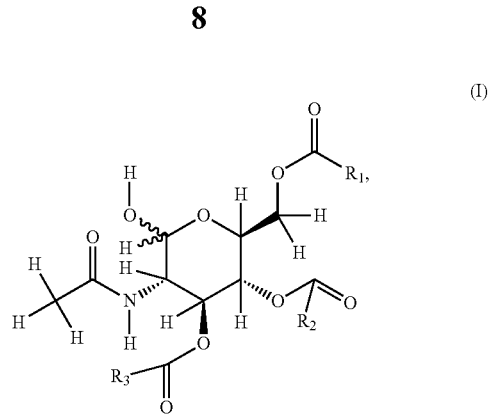

a compound of formula II:

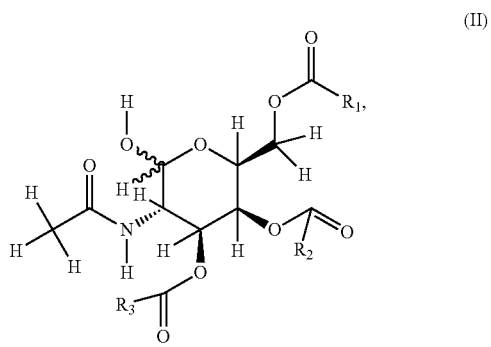

a compound of formula III:

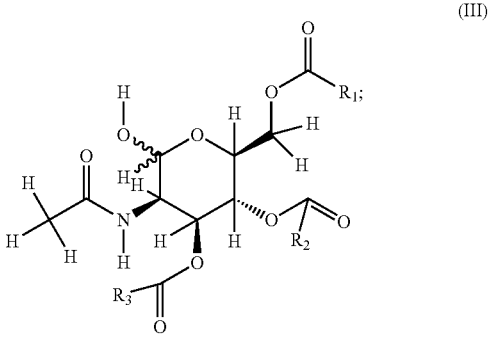

wherein $R_1$, $R_2$, and $R_3$ are the same or different, and are $C_1$-$C_6$ alkyl substituents.

It will be understood by those of ordinary skill in the art that the compounds of formulas I-III are based on the derivitization of the core GlcNAc, GalNAc and ManNAc moieties respectfully.

In accordance with another embodiment, the present invention provides a method for treating joint disease in a mammal comprising: a) administering to the cartilage in need of treatment a composition comprising the compounds of formulas I-III, wherein $R_1$, $R_2$, and $R_3$ of the compounds of formulas I-III are $C_3$ alkyl groups and are selected from group consisting of:

(compound 1)

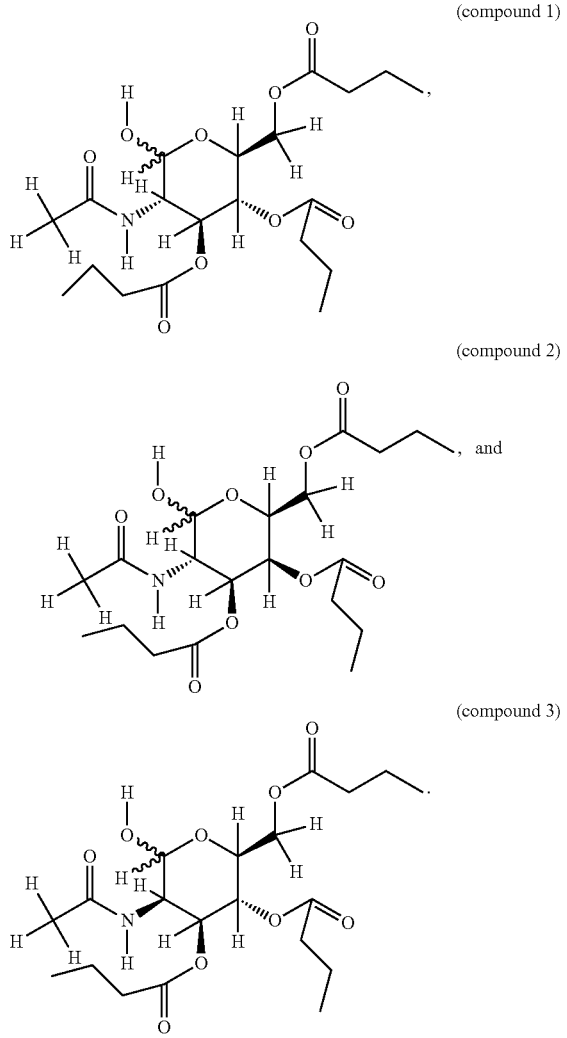

(compound 2)

(compound 3)

In accordance with a further embodiment, the present invention provides a pharmaceutical composition comprising the compounds disclosed herein, and a pharmaceutically acceptable carrier.

In accordance with an embodiment, the present invention provides a method for treating joint disease in a mammal comprising: a) administering to the cartilage in need of treatment a composition comprising a compound of formula I:

(I)

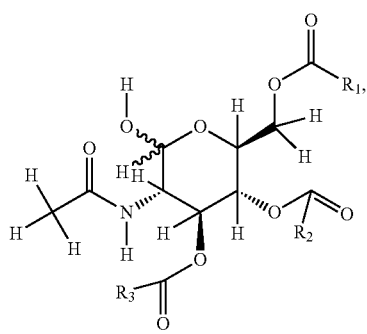

a compound of formula II:

(II)

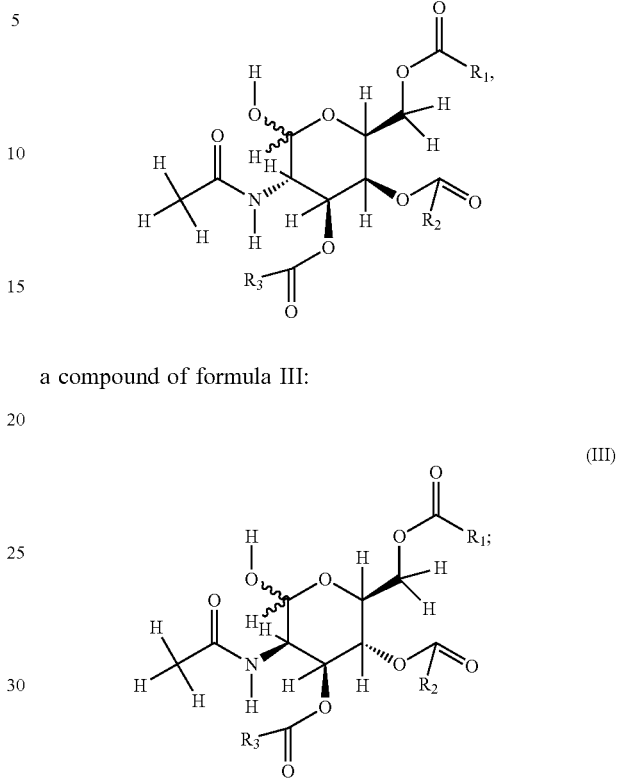

a compound of formula III:

(III)

wherein $R_1$, $R_2$, and $R_3$ are the same or different, and are $C_1$-$C_6$ alkyl substituents.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure. As used herein, the compositions comprise hexosamines which are modified with short chain alkyl groups. Preferably alkyl groups between 2 to 6 carbons which may, or may not be substituted.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl and so on.

The definition of each expression, e.g., alkyl, aryl etc., when it occurs more than once in any structure, is intended to be independent of its definition elsewhere in the same structure unless otherwise indicated expressly or by the context.

It will be understood that "substitution" or "substituted with" includes the implicit proviso that such substitution is in accordance with the permitted valency of the substituted atom and the substituent, and that the substitution results in a stable compound, e.g., which does not spontaneously undergo transformation, such as by rearrangement, cyclization, elimination, or other reaction.

In accordance with a further embodiment, the present invention provides a method for treating joint disease in a mammal comprising any of the compositions described above in a biocompatible hydrogel.

By "hydrogel" is meant a water-swellable polymeric matrix that can absorb water to form elastic gels, wherein "matrices" are three-dimensional networks of macromolecules held together by covalent or noncovalent crosslinks. On placement in an aqueous environment, dry hydrogels swell by the acquisition of liquid therein to the extent allowed by the degree of cross-linking.

A biologically compatible polymer refers to a polymer which is functionalized to serve as a composition for creating an implant. The polymer is one that is a naturally occurring polymer or one that is not toxic to the host. The polymer can, e.g., contain at least an imide. The polymer may be a homopolymer where all monomers are the same or a heteropolymer containing two or more kinds of monomers. The terms "biocompatible polymer," "biocompatible cross-linked polymer matrix" and "biocompatibility" when used in relation to the instant polymers are art-recognized are considered equivalent to one another, including to biologically compatible polymer. For example, biocompatible polymers include polymers that are neither toxic to the host (e.g., an animal or human), nor degrade (if the polymer degrades at a rate that produces monomeric or oligomeric subunits or other byproducts at toxic concentrations in the host).

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, and star polymers.

A monomer is the basic repeating unit in a polymer. A monomer may itself be a monomer or may be dimer or oligomer of at least two different monomers, and each dimer or oligomer is repeated in a polymer.

A polymerizing initiator refers to any substance that can initiate polymerization of monomers or macromers by, for example, free radical generation. The polymerizing initiator often is an oxidizing agent. Exemplary polymerization initiators include those which are activated by exposure to, for example, electromagnetic radiation or heat.

This disclosure is directed, at least in part, to polymers, matrices, and gels, and methods of making and using matrices, polymers and gels having the modified hexosamine analogs described above. Gels, networks, scaffolds, films and the like of interest made with the composition(s) of interest encourage cell, tissue and organ integration and growth. The optional presence of cells, such as stem cells, enhances cell, tissue, and organ integration and growth.

As used herein, the term "joint disease" means any deterioration or defect in the cartilage of a subject, including, for example, joints, the synovium and bone to which cartilage is a component.

The instant invention provides for ex vivo polymerization techniques to form scaffolds and so on that can be molded to take the desired shape of the defect, promote tissue development by stimulating native cell repair, and can be potentially implanted by minimally invasive injection.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

In accordance with yet another embodiment, the present invention provides a method for treating joint disease in a mammal comprising any of the compositions described above in a biocompatible hydrogel and at least one additional biologically active agent.

Biocompatible polymer, biocompatible cross-linked polymer matrix and biocompatibility are art-recognized. For example, biocompatible polymers include polymers that are neither themselves toxic to the host (e.g., and animal or human), nor degrade (if the polymer degrades) at a rate that produces monomeric or oligomeric subunits or other byproducts at toxic concentrations in the host. In certain embodiments of the present invention, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

"Biodegradable" is art-recognized, and includes monomers, polymers, polymer matrices, gels, compositions and formulations, such as those described herein, that are intended to degrade during use, such as in vivo. Biodegradable polymers and matrices typically differ from non-biodegradable polymers in that the former may be degraded during use. In certain embodiments, such use involves in vivo use, such as in vivo therapy, and in other certain embodiments, such use involves in vitro use. In general, degradation attributable to biodegradability involves the degradation of a biodegradable polymer into its component subunits, or digestion, e.g., by a biochemical process, of the polymer into smaller, non-polymeric subunits. In certain embodiments, two different types of biodegradation may generally be identified. For example, one type of biodegradation may involve cleavage of bonds (whether covalent or otherwise) in the polymer backbone. In such biodegradation, monomers and oligomers typically result, and even more typically, such biodegradation occurs by cleavage of a bond connecting one or more of subunits of a polymer. In contrast, another type of biodegradation may involve cleavage of a bond (whether covalent or otherwise) internal to a side chain or that connects a side chain, functional group and so on to the polymer backbone. For example, a therapeutic agent, biologically active agent, or other chemical moiety attached as a side chain to the polymer backbone may be released by biodegradation. In certain embodiments, one or the other or both general types of biodegradation may occur during use of a polymer. As used herein, the term "biodegradation" encompasses both general types of biodegradation.

The degradation rate of a biodegradable polymer often depends in part on a variety of factors, including the chemical identity of the linkage responsible for any degradation, the molecular weight, crystallinity, biostability, and degree of cross-linking of such polymer, the physical characteristics of the implant, shape and size, and the mode and location of administration. For example, the greater the molecular weight, the higher the degree of crystallinity, and/or the greater the biostability, the biodegradation of any biodegradable polymer is usually slower. The term "biodegradable" is intended to cover materials and processes also termed "bioerodible."

In certain embodiments, the biodegradation rate of such polymer may be characterized by the presence of enzymes, for example, a chondroitinase. In such circumstances, the biodegradation rate may depend on not only the chemical identity and physical characteristics of the polymer matrix, but also on the identity of any such enzyme.

In certain embodiments, polymeric formulations of the present invention biodegrade within a period that is acceptable in the desired application. In certain embodiments, such as in vivo therapy, such degradation occurs in a period usually less than about five years, one year, six months, three months, one month, fifteen days, five days, three days, or even one day on exposure to a physiological solution with a pH between 6 to 8 having a temperature of between about 25° C. to 37° C. In other embodiments, the polymer degrades in a period of between about one hour and several weeks, depending on the desired application. In some embodiments, the polymer or polymer matrix may include a detectable agent that is released on degradation.

Cross-linked herein refers to a composition containing intermolecular cross-links and optionally intramolecular cross-links, arising from, generally, the formation of covalent bonds. Covalent bonding between two cross-linkable components may be direct, in which case an atom in one component is directly bound to an atom in the other component, or it may be indirect, through a linking group. A cross-linked gel or polymer matrix may, in addition to covalent, also include intermolecular and/or intramolecular noncovalent bonds such as hydrogen bonds and electrostatic (ionic) bonds.

"Gel" refers to a state of matter between liquid and solid, and is generally defined as a cross-linked polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface).

Hydrogels consist of hydrophilic polymers cross-linked to from a water-swollen, insoluble polymer network. Cross-linking can be initiated by many physical or chemical mechanisms. Photopolymerization is a method of covalently crosslink polymer chains, whereby a photoinitiator and polymer solution (termed "pre-gel" solution) are exposed to a light source specific to the photoinitiator. On activation, the photoinitiator reacts with specific functional groups in the polymer chains, crosslinking them to form the hydrogel. The reaction is rapid (3-5 minutes) and proceeds at room and body temperature. Photoinduced gelation enables spatial and temporal control of scaffold formation, permitting shape manipulation after injection and during gelation in vivo. Cells and bioactive factors can be easily incorporated into the hydrogel scaffold by simply mixing with the polymer solution prior to photogelation.

Hydrogels of interest can be semi-interpenetrating networks that promote cell, tissue and organ repair while discouraging scar formation. The hydrogels of interest also are configured to have a viscosity that will enable the gelled hydrogel to remain affixed on or in the cell, tissue or organ, or surface. Viscosity can be controlled by the monomers and polymers used, by the level of water trapped in the hydrogel, and by incorporated thickeners, such as biopolymers, such as proteins, lipids, saccharides and the like. An example of such a thickener is hyaluronic acid or collagen.

"Incorporated," "encapsulated," and "entrapped" are art-recognized when used in reference to a therapeutic agent, dye, or other material and a polymeric composition, such as a composition of the present invention. In certain embodiments, these terms include incorporating, formulating or otherwise including such agent into a composition that allows for sustained release of such agent in the desired application. The terms may contemplate any manner by which a therapeutic agent or other material is incorporated into a polymer matrix, including, for example, attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved in the polymer. Any form of encapsulation or incorporation is contemplated by the present invention, in so much as the sustained release of any encapsulated therapeutic agent or other material determines whether the form of encapsulation is sufficiently acceptable for any particular use.

It will be understood by those of ordinary skill that the polymers used in the inventive compositions and methods can be in many useful forms, including, but not limited to, hydrogels, fibers, nanofibers, sponges, etc.

A functional group or a moiety which can be used for substitution is one capable of mediating formation of a polymer or reaction with a surface or other molecule. Functional groups include the various radicals and chemical entities taught herein, and include alkenyl moieties such as acrylates, methacrylates, dimethacrylates, oligoacrylates, oligomethacrylates, ethacrylates, itaconates or acrylamides. Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrile and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene, and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid, and styrene carboxylic acid. Suitable polyethylenically unsaturated monomers include butadiene, isoprene, allylmethacrylate, diacrylates of alkyl diols such as butanediol diacrylate and hexanediol diacrylate, divinyl benzene, and the like.

In some embodiments, a monomeric unit of a biologically compatible polymer may be functionalized through one or more thio, carboxylic acid or alcohol moieties located on a monomer of the biopolymer. For example, in the case of chondroitin sulfate, a carbonyl group can be derivatized with a imide group using, for example, carbodiimide chemistry. An alcohol group can be derivatized using, for example, the Mitsunobu reaction, Procter et al., Tetra. Lett. 47(29): 5151-5154, 2006.

Cross-linked polymer matrices of the present invention may include and form hydrogels. The water content of a hydrogel may provide information on the pore structure. Further, the water content may be a factor that influences, for example, the survival of encapsulated cells within the hydrogel. The amount of water that a hydrogel is able to absorb may be related to the cross-linking density and/or pore size. For example, the percentage of imides on a functionalized macromer, such as chondroitin sulfate, hyaluronic acid, dextran, carboxy methyl starch, keratin sulfate, or ethyl cellulose, may dictate the amount of water that is absorbable.

The compositions of the present invention may comprise monomers, macromers, oligomers, polymers, or a mixture thereof. The polymer compositions can consist solely of covalently crosslinkable polymers, or ionically crosslinkable polymers, or polymers crosslinkable by redox chemistry, or polymers crosslinked by hydrogen bonding, or any combination thereof. The reagents should be substantially hydrophilic and biocompatible.

Suitable hydrophilic polymers useful in the hydrogels of the present invention include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly (propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as Ficoll™, polysucrose, hyaluronic acid, dextran, heparan sulfate, chondroitin sulfate, heparin, or alginate, and proteins such as gelatin, collagen, albumin, or ovalbumin, carboxy methyl starch, or copolymers or blends thereof. As used herein, "celluloses" includes cellulose and derivatives of the types described above; "dextran" includes dextran and similar derivatives thereof.

Methods for the synthesis of the polymers described above are known to those skilled in the art, see, e.g., Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available. Naturally occurring polymers can be isolated from biological sources as known in the art or are commercially available. Naturally occurring and synthetic polymers may be modified using chemical reactions available in the art and described, for example, in March, "Advanced Organic Chemistry," 4th Edition, 1992, Wiley-Interscience Publication, New York.

Numerous chemical options are available for modifying polymers that may then undergo a radical polymerization. For example, methacrylic anhydride, methacryloyl chloride and glycidyl methacrylate may be used to add methacrylate groups to one or more monomers of a polymer chain. Glycidyl methacrylate may be used, for example, for efficiency of reaction. Further, the modification reagents may be chosen to optimize a lack of cytotoxic byproducts.

Polymerization initiators can also be used and are described, e.g., in U.S. Patent Application Publication No. 2010/0137241, which is incorporated by reference in entirety.

Cross-linked polymer matrices of the present invention may form and may include hydrogels. The water content of a hydrogel may provide information on the pore structure. Further, the water content may be a factor that influences, for example, the survival of encapsulated cells within the hydrogel. The amount of water that is able to be absorbed may be related to the cross-linking density pore size. For example, the percentage of methacrylate groups on a functionalized polymer may dictate the amount of water absorbable.

The mechanical properties of a cross-linked polymer matrix, such as a scaffold, may also be related to the pore structure. For applications in tissue engineering, scaffolds with different mechanical properties may be desirable depending on desired clinical application. For example, scaffolds for cartilage tissue engineering in the articular joint must survive higher mechanical stresses than a cartilage tissue engineering system in other body sites. Thus, polymers with mechanical properties that are easily manipulated may be desired, and can be obtained as a design choice.

Cytotoxicity of the biopolymer scaffold system may be evaluated with any suitable cells, such as fibroblasts, by, for example, using a live-dead fluorescent cell assay and MTT, a compound that actively metabolizing cells convert from yellow to purple, as taught hereinabove, and as known in the art.

In one aspect of this invention, a composition comprising a cross-linked polymer matrix or gel and one or more biologically active agents may be prepared. The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in cross-linked polymer matrix of this invention, to, for example, promote cartilage formation. In other embodiments, a biologically active agent may be used in cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In certain embodiments, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility or for the resulting physical properties of the reagents, the setting or gelling matrix or the set or gelled matrix.

Buffers, acids and bases may be incorporated in the compositions to adjust pH. Agents to increase the diffusion distance of agents released from the composition may also be included.

The charge, lipophilicity or hydrophilicity of a composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM.

The formulations to be used for in vivo administration must be sterile. That can be accomplished, for example, by filtration through sterile filtration membranes. For example, the formulations of the present invention may be sterilized by filtration.

The biopolymer composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the biopolymer to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease. For example, a treatment of interest can increase the use of a joint in a host, based on baseline of the injured or diseases joint, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent of interest reduces the symptoms of a disease, such as a symptom of arthritis by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

Biologically active agents and other additives may be incorporated into the cross-linked synthetic polymer composition by admixture or added to a reagent preparation. Alternatively, the agents may be incorporated into the cross-linked polymer composition by admixture or added to a reagent preparation. Alternatively, the agents may be incorporated into the cross-linked polymer matrix by binding these agents to the functional groups on the polymers of interest. Such compositions may include linkages that can be easily biodegraded, for example as a result of enzymatic degradation, resulting in the release of the active agent or additive into the target tissue, where it will exert its desired therapeutic effect.

A simple method for incorporating biologically active agents containing nucleophilic groups into the cross-linked polymer composition involves mixing the active agent with a polyelectrophilic component. By varying the relative molar amounts of the different components of the reactive composition, it is possible to alter the net charge of the resulting cross-linked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

The cross-linked polymer matrix compositions of the present invention can also be used to deliver various types of living cells (e.g., a mesenchymal stem cell, a cardiac stem cell, a liver stem cell, a retinal stem cell, and an epidermal stem cell) or genes to a desired site of administration to form new tissue. The term "genes" as used herein is intended to encompass genetic material from natural sources, synthetic nucleic acids, DNA, antisense DNA and RNA.

The cells may be either allogeneic or xenogeneic in origin. The compositions can be used to deliver cells of species that are genetically modified.

In accordance with an embodiment, the present invention provides the use of a pharmaceutical composition comprising:

a compound of formula I:

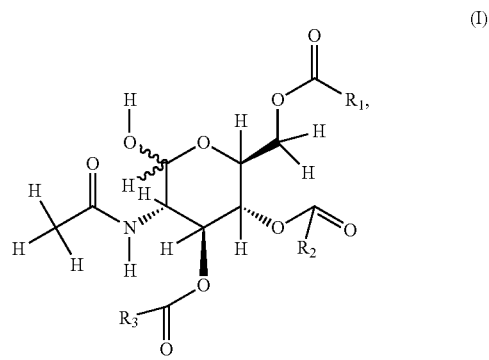

a compound of formula II:

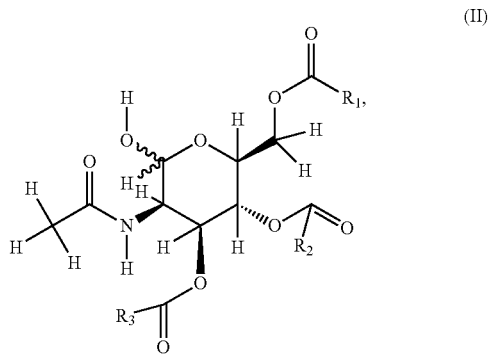

a compound of formula III:

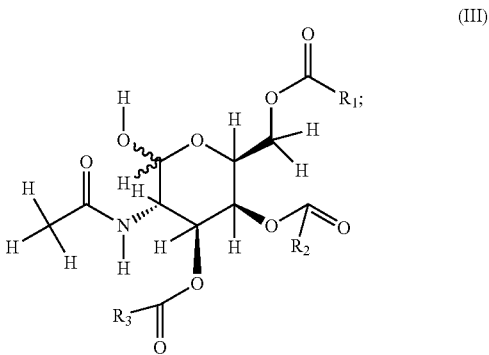

wherein $R_1$, $R_2$, and $R_3$ are the same or different, and are $C_1$-$C_6$ alkyl substituents, and a pharmaceutically acceptable carrier, in an effective amount, as a medicament for the treatment of a joint disease in a mammal.

In accordance with some embodiments, the present invention provides the use of the compounds of formulas I, II or III, wherein $R_1$, $R_2$, and $R_3$ of the compounds of formulas I-III are the same.

In accordance with some embodiments, the present invention provides the use of the compounds of formulas I, II or III, wherein $R_1$, $R_2$, and $R_3$ of the compounds of formulas I-III are $C_4$ alkyl groups and are selected from group consisting of:

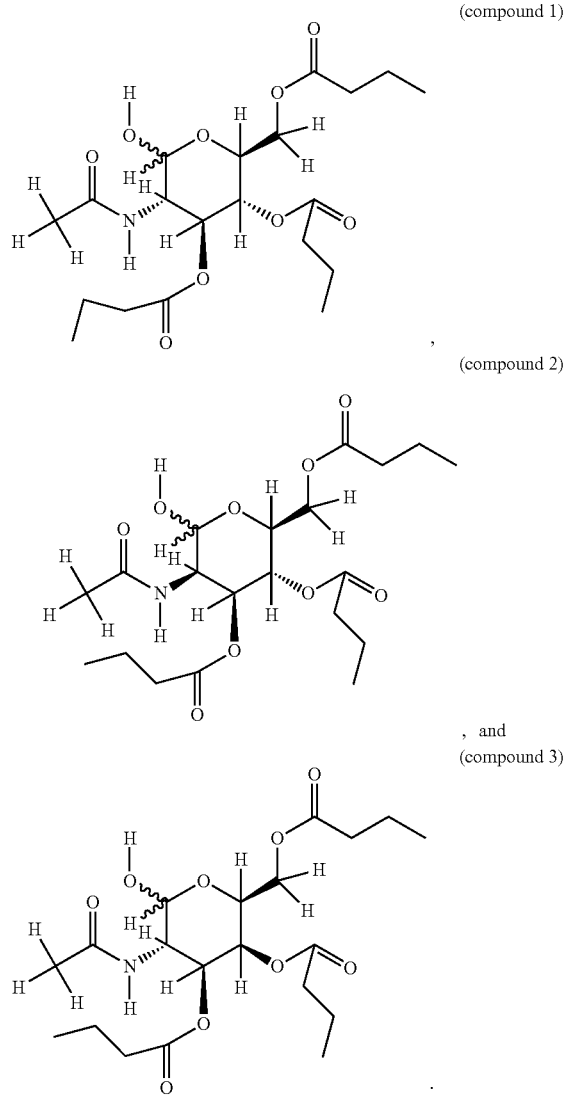

In accordance with some embodiments, the present invention provides the use of the compounds of formulas I, II or III, wherein the composition further comprises a biocompatible hydrogel.

In accordance with some embodiments, the present invention provides the use of the compounds of formulas I, II or III, wherein the composition further comprises a biocompatible hydrogel and the biocompatible hydrogel is a cross-linked hydrophilic polymer matrix.

In accordance with some embodiments, the biocompatible polymer is in the form of hydrogels, fibers, nanofibers and sponges, and are selected from the group consisting of: Poly(ethylene glycol), Poly(propylene glycol), Poly(methyl vinyl ether), Oligoethylene, Poly(isobutylene) Poly(tetrahydrofuran) Poly(oxytrimethylene), Poly(dimethylsiloxane), Poly(dimethylsilane), Nylon 6, Nylon 11, Poly(acrylonitrile), Squalane, Poly(1,3-dioxolane), Poly(iminooligomethylene), Poly(1-lysine), Polyethyleneimine, Poly(adipate), Poly(1-caprolactone), Poly(L-lactic acid), or derivatives thereof.

In accordance with some embodiments, the present invention provides the use of the compounds of formulas I, II or II, wherein the compounds are present in the composition and concentration of between about 1 µM to about 300 µM.

In accordance with some embodiments, the present invention provides the use of the compounds of formulas I, II or II, wherein the composition further comprises a second biologically active agent.

In accordance with some embodiments, the present invention provides the use of the compounds of formulas I, II or II, wherein the use increases extracellular matrix accumulation in chondrocytes stimulated by IL-1β.

In accordance with some embodiments, the present invention provides the use of the compounds of formulas I, II or II, wherein the use decreases NFKB1 gene expression in chondrocytes stimulated by IL-1β.

In some embodiments, the compositions of the invention may not easily be degraded in vivo. Thus, cells entrapped within the cross-linked polymer matrix compositions will be isolated from the host cells and, as such, will not provoke or will delay an immune response in the host.

In some embodiments, compositions disclosed herein may be positioned in a surgically created defect that is to be reconstructed, and is to be left in that position after the reconstruction has been completed. The present invention may be suitable for use with local tissue reconstructions, pedicle flap reconstructions, corneal flap sealings or free flap reconstructions.

In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any surgically acceptable patch or implant, if needed.

EXAMPLES

Synthesis of Monosaccharide Hybrid Molecules. Molecules were synthesized as previously reported (3,4,6-O-Bu₃ManNAc (ACS Chem Bio 3: 230-240 (2008)), 3,4,6-O-Bu₃GlcNAc (J Med Chem 51: 8135-8147 (2008)) and 3,4,6-O-Bu₃GalNAc (J Med Chem 52: 2515-2530 (2009)), denoted as ManNAc-a, GlcNAc-a and GalNAc-a, respectively). To synthesize 3,4,6-O-Bu₃GlcNAc the intermediate molecule 2-acetamido-1,3,4,6-tetra-O-acyl-2-deoxy-α,β-D-glucopyranose (1,3,4,6-O-Bu₃GlcNAc) was synthesized. Briefly, to a stirring solution of GlcNAc (2.2 mmol) in pyridine (2.0 ml) at 21° C. butyric anhydride (15.6 mmol) and 4-(dimethylamino) pyridine (cat.) was added. After 24 hours, the mixture was concentrated under vacuum and co-concentrated with toluene (25 ml). The residue was dissolved in methylene chloride (100 ml), washed with cold aqueous HCl (0.5 N, 100 ml), water (100 ml), and saturated NaHCO₃ (100 ml). The organic layer was filtered and concentrated. Column chromatography of the residue (hexanes/ethyl acetate) on silica gel provided the per-acyl compounds in the form of syrups that crystallized upon standing. To synthesize 3,4,6-O-Bu₃GlcNAc, the 2-acetamido-1,3,4,6-tetra-O-acyl-2-deoxy-α,β-D-glucopyranose (2.0 mmol) was mixed with activated and powdered molecular sieves 4 Å (4.0 g) in methanol (100 ml) and stirred at 22° C. The reaction mixture was monitored by TLC {hexanes: ethyl acetate (AcOEt)} to maximize conversion to the hemiacetal while minimizing de-acylation at positions other than C1. After ~7-12 hours, the reaction mixture was filtered through a pad of celite, washed twice with methanol (10 ml)

and the combined filtrate was concentrated. Column chromatography of the residue (hexanes:ethyl acetate (AcOEt)) was done to separate unreacted starting material, respectively from the hemiacetals.

To synthesize 1,3,4-O-Bu$_3$GlcNAc, to a stirred mixture of GlcNAc (0.835 mmol) in pyridine (2.7 ml) was added triphenylmethyl chloride (3.0 g, 1.07 mmol) at 22° C. After 48 hours, the reaction mixture was heated at 60° C. for 1.0 hour and monitored by TLC (AcOEt). The reaction mixture was concentrated with toluene (3×20 ml). The residue was dissolved in AcOEt and washed with water. The organic layers were collected, dried over anh. Na$_2$SO$_4$, filtered and concentrated to obtain 2-Acetamido-2-deoxy-6-O-triphenylmethyl-α,β-D-glucopyranose as a crude product which was taken to the next step without further purification. To the crude product (2.16 mmol) in pyridine (1.46 ml, 18 mmol) at 0° C. (ice-water bath), butyric anhydride (12 mmol) was added. The reaction mixture was allowed to warm to 22° C. and monitored by TLC (hexanes:AcOEt 3:1). After 24 hours, the mixture was concentrated with toluene (3×10 ml), and extracted using a mixture of dichloromethane (100 ml) and water (50 ml). The organic layers were collected, dried over anh. Na$_2$SO$_4$, filtered and concentrated. Column chromatography of the residue (hexanes:AcOEt) gave 2-Acetamido-1,3,4-tri-O-butanoyl-2-deoxy-6-O-triphenylmethyl-α,β-D-glucopyranose. A stirred mixture of 2-Acetamido-1,3,4-tri-O-butanoyl-2-deoxy-6-O-triphenylmethyl-α,β-D-glucopyranose (0.743 mmol) in 80% aqueous acetic acid (10 ml) was heated at 60° C. and monitored by TLC (hexanes:AcOEt). After ~4 hours, the reaction mixture was concentrated with toluene (3×10 ml). Column chromatography of the residue (hexanes:AcOEt) gave 1,3,4-O-Bu$_3$GlcNAc (as a mixture of anomers). Compounds were maintained at −20° C. after lyophilization. Stock solutions used for experiments were made periodically by dissolving analog in 100% ethanol at a concentration of 100 mM; stock solutions were and stored at 4° C. for up to up to three months.

Cell Isolation and Culturing. Bovine chondrocytes were isolated from 4- to 8-week-old calves (Research 87, Inc., Boylston, Mass.), as previously described. Briefly, cartilage was dissected from the femoral patellar groove and condyles and minced into approximately 1 mm$^2$ pieces. Cells were isolated from the tissue by digesting overnight at 37° C. with 2 mg/ml type II collagenase (Worthington Biochemical Corp., Lakewood, N.J.), 5% fetal bovine serum (FBS), 100 U/ml penicillin and 100 µg/ml streptomycin on an orbital shaker. The cell suspension was passed through a 70 µm cell strainer, followed by centrifugation. Cells were washed 3 times using sterile phosphate buffered saline (PBS). Chondrocyte medium was composed of high glucose Dulbecco's Modified Eagle's Medium (DMEM) supplemented with 10 mM HEPES, 0.4 mM L-proline, 50 µg/ml ascorbic acid, 10% (v/v) fetal bovine serum (FBS; Hyclone Laboratories, Inc., Logan, Utah), 0.1 mM non-essential amino acids, 100 U/ml penicillin and 100 µg/ml streptomycin.

Goat MSCs were isolated from 2- to 4-year-old goats (Thomas D. Morris, Inc., Reisterstown, Md.), as previously described. Briefly, bone marrow aspirates treated with 6,000 U/ml heparin were washed twice with PBS. Cells were plated at a density of 120,000 mononuclear cells/cm$^2$ and cultured in high glucose DMEM supplemented with 10% (v/v) FBS, 2 mM L-glutamine, 100 U/ml penicillin and 100 µg/ml streptomycin. The following day, tissue culture dishes were washed with PBS and medium was replaced. Medium changes were performed 3 times per week. Cells were passaged using 0.25% trypsin. They were used for experiments after passage four.

Metabolic Activity/Toxicity Screening: Water Soluble Tetrazonium-1 (WST-1) Assay. Chondrocytes were plated in 96-well plates at 10,000 cells/well. Cells were allowed to adhere and spread for 3 days, after which medium was changed to medium containing hexosamine analogs at concentrations ranging from 0 µM-320 µM and cultured for an additional 3 days. The WST-1 assay (Roche Molecular Biochemicals, Mannheim, Germany) was used to determine cell proliferation in the presence of sugar analog following the manufacturer's protocol. Briefly, medium was aspirated from each well and the wells were washed with sterile PBS. One hundred microliters of WST-1 working solution was added to each well and 6 empty wells for background subtraction. The WST-1 reagent was incubated with the cells for 3-4 hours, during which time, the enzymatic cleavage of the tetrazolium salt WST-1 to formazan by cellular mitochondrial dehydrogenases resulted in a visible light color shift in the medium. Absorbance of the wells was read using a microplate reader at a wavelength of 450 nm. The absorbance of the wells containing WST-1 reagent with no cells was subtracted from the absorbance readings. Data is presented as the background subtracted reading normalized to 0 µM wells from five independent experiments for each hexosamine analog.

Monolayer cell culture. In some experiments, cells were plated in 6-well plates at 1×10$^6$ cells/well and allowed to adhere for 24 hours in the presence or absence of 10 ng/ml IL-1β. After 24 hours, medium was changed to medium supplemented with or without 50 µM 3,4,6-O-Bu$_3$GlcNAc with the respective IL-1β concentration and incubated for an additional 4 hours or 24 hours.

Photoencapsulation in Poly(Ethylene Glycol)-Diacrylate (PEGDA) Hydrogels and Construct Culturing. For all 3D culture experiments, cells were photoencapsulated in PEGDA hydrogels, as previously described. Briefly, 100 mg PEGDA (3.4 kDa, SunBio, Anyang City, South Korea) was dissolved in 1 ml sterile PBS. A photoinitiator solution of Irgacure® 2959 (CIBA Specialty Chemicals) was prepared by dissolving 100 mg of Irgacure® 2959 in 1 ml 70% ethanol. Five microliters of the Irgacure® 2959 solution was added to 1 ml of PEGDA solution. Cells were suspended in the hydrogel precursor solution at a density of 20 million cells/ml and polymerized in sterile molds. A high cell density was chosen as it has been shown. Based on our previous studies a high cell density was chosen to best to support a cell phenotype and differentiation and cell phenotype. Polymerization was carried out using UV light (365 nm, 3.2 mW/cm$^2$) exposure for 5 minutes.

For chondrocyte experiments, the cell-laden hydrogels were cultured in chondrocyte medium supplemented with 10 ng/ml IL-1β for 3 days. Following the initial 3 days, constructs were cultured with medium containing specific concentrations of hexosamine analog with 10 ng/ml IL-1β for an additional 21 days. The medium was changed 3 times per week.

For chondrogenesis experiments, the cell-laden hydrogels were cultured in chondrogenic induction medium (high glucose DMEM supplemented with 50 µg/ml ascorbic acid-2-phosphate, 40 µg/ml L-proline, 100 µg/ml sodium pyruvate, 1% ITS-premix (6.25 µg/ml insulin, 6.25 µg/ml transferrin, 6.25 ng/ml selenous acid, 1.25 mg/ml bovine serum albumin (BSA), 5.35 µg/ml linoleic acid (Collaborative Biomedical, BD Bioscience, Bedford, Mass.)) and 10 ng/ml TGF-β1 (Fitzgerald Industries International, Acton, Mass.) with specified concentrations of GalNAc-a or 100 nM dexamethasone (as a control). Constructs were cultured for 21 days with medium changes 3 times per week. For IL-1β stimulation, the cell-laden hydrogels were cultured for 3 days in chondrogenic induction medium supplemented with 10 ng/ml IL-1β. Constructs were cultured for an additional 21 days with chondrogenic induction medium supplemented with 10 ng/ml IL-1β and the specified concentration of GalNAc-a.

Biochemical Analysis. The constructs (n=3 for chondrocyte experiments and n=4 for chondrogenic experiments) were lyophilized for 48 hours and the dry weights measured. Constructs were then homogenized in 125 μg/ml papainase (Worthington Biochemical Corp., Lakewood, N.J.) and digested for 16 hours at 60° C. Quantification of DNA content was carried out using a Hoescht Dye 33342 DNA assay. Calf thymus DNA was used to generate standard curves. Quantification of sulfated glycosaminoglycans (sGAG), a molecule found in cartilage ECM, was carried out using a 1,9-dimethylmethylene blue (DMMB) dye assay; chondroitin sulfate was used to generate standard curves. Quantification of collagen was carried out via measuring hydroxyproline content after hydrolyzing in 6 N HCl overnight at 120° C. The reaction of hydroxyproline with chloramine-T and p-dimethylaminobenzaldehyde was performed as a measure of total collagen content; hydroxyproline was used to generate standard curves.

Histology and Immunohistochemistry. Constructs were fixed in 10% formalin or 4% paraformaldehyde followed by dehydration in increasing concentrations of ethanol, embedded in paraffin and sliced into 5 μm sections. After paraffin removal and subsequent rehydration, sections were stained for proteoglycans using Safranin-O and fast green or prepared for immunohistochemistry. For immunohistochemical staining of type II collagen, endogenous peroxidase was quenched using 3% (v/v) hydrogen peroxide in methanol. Sections were then incubated at 37° C. with 2.5% (w/v) hyaluronidase and stained using a Histostain-SP Kit (AEC, Broad Spectrum) (Life Technologies, Grand Island, N.Y.) following the manufacturer's instructions. Primary antibody for type II collagen (Fitzgerald Industries International, Acton, Mass.) was used at a dilution of 1:100 in 1% (w/v) BSA dissolved in PBS.

RNA Isolation and Real-Time PCR. Total RNA was extracted using TRIzol® reagent (Life Technologies, Grand Island, N.Y.) following the manufacturer's protocol. cDNA was synthesized using Superscript® II reverse transcriptase (Life Technologies, Grand Island, N.Y.) following the manufacturer's protocol. Real-time PCR was carried out using a StepOnePlus™ Real-Time PCR System (Life Technologies, Grand Island, N.Y.). mRNA amounts for bovine primers were calculated using the ΔΔCt method. Relative mRNA quantities for goat primers were calculated using the Pfaffl method. The PCR primers used are listed in Tables 1 and 2.

TABLE 1

List of bovine primers used for real-time PCR

| Gene | Sequence |
|---|---|
| Aggrecan | F-CATCGGGCTTGCCAGAGTT (SEQ ID NO: 1) |
|  | R-ACTGGTGTCCACGAACGTAATG (SEQ ID NO: 2) |
| Type I Collagen | F-GGGCAACAGCAGATTCACTTAC (SEQ ID NO: 3) |
|  | R-CAAGGATAGGCAGGCGAGAT (SEQ ID NO: 4) |
| Type II Collagen | F-GCAACCCTGGAACTGATGGA (SEQ ID NO: 5) |
|  | R-GCTCACCCGTTTGACCTTTT (SEQ ID NO: 6) |
| IκBα | F-GCAGGCCACCAACTACAATG (SEQ ID NO: 7) |
|  | R-AGTGACACCAGGTCGGGATT (SEQ ID NO: 8) |
| NFκB1 | F-TTACAAAACCAGCCTCCGTG (SEQ ID NO: 9) |
|  | R-GCCGAAACTGTCCGAGAAA (SEQ ID NO: 10) |
| MMP9 | F-TAGCACGCACGACATCTTTC (SEQ ID NO: 11) |
|  | R-GAAGGTCACGTAGCCCACAT (SEQ ID NO: 12) |
| MMP13 | F-GCTCACGCTTTCCCTCCT (SEQ ID NO: 13) |
|  | R-CAAACTCATGGGCAGCAACA (SEQ ID NO: 14) |
| ADAMTS4 | F-TCGAAGCCGGGACAGGGAGG (SEQ ID NO: 15) |
|  | R-CCTCCCGGGATGCGAGTCCA (SEQ ID NO: 16) |
| ADAMTS5 | F-TCACTGCCTACTTAGCCCTGAA (SEQ ID NO: 17) |
|  | R-GCTCCAACCGCTGTAGTTCAT (SEQ ID NO: 18) |
| IL-1β | F-CGTCTTCCTGGGACATTTTCG (SEQ ID NO: 19) |
|  | R-TGCCAGTCCTCGGGGTTATT (SEQ ID NO: 20) |
| TNFα | F-ACACCATGAGCACCAAAAGC (SEQ ID NO: 21) |
|  | R-GCAACCAGGAGGAAGGAGAA (SEQ ID NO: 22) |
| iNOS | F-CCGCTCCCGTCCTTGCATCC (SEQ ID NO: 23) |
|  | R-CCGCCCTGGAGCCCTTTGTG (SEQ ID NO: 24) |
| PTGES | F-TGCCTCAGAGCCCACCGGAAT (SEQ ID NO: 25) |
|  | R-AGTGCATCCGGGCGACGAAG (SEQ ID NO: 26) |
| Beta Actin | F-TGGCACCACACCTTCTACAATGAGC (SEQ ID NO: 27) |
|  | R-GCACAGCTTCTCCTTAATGTCACGC (SEQ ID NO: 28) |

TABLE 2

List of goat primers used for real-time PCR

| Gene | Sequence | Efficiency (%) |
|---|---|---|
| Aggrecan | F-CACGATGCCTTTCACCACGAC (SEQ ID NO: 28) | 90 |
|  | R-TGCGGGTCAACAGTGCCTATC (SEQ ID NO: 29) |  |
| Type I Collagen | F-AGGGCCAAGACGAAGACATC (SEQ ID NO: 30) | 84 |
|  | R-AGATCACGTCATCGCACAACA (SEQ ID NO: 31) |  |
| Type II Collagen | F-GTGGAGCAGCAAGAGCAAGGA (SEQ ID NO: 32) | 63 |
|  | R-CTTGCCCCACTTACCAGTGTG (SEQ ID NO: 33) |  |
| SOX9 | F-TTCATGAAGATGACCGACGA (SEQ ID NO: 34) | 90 |
|  | R-CACACCATGAAGGCGTTCAT (SEQ ID NO: 35) |  |

TABLE 2-continued

List of goat primers used for real-time PCR

| Gene | Sequence | Efficiency (%) |
|---|---|---|
| MMP13 | F-GCTCACGCTTTCCCTCCT (SEQ ID NO: 36)<br>R-CAAACTCATGGGCAGCAACA (SEQ ID NO: 38) | 97 |
| Beta Actin | F-TGGCACCACACCTTCTACAATGAGC (SEQ ID NO: 39)<br>R-GCACAGCTTCTCCTTAATGTCACGC (SEQ ID NO: 40) | 80 |

Statistical Analysis. Data are expressed as mean±standard deviation (SD) for biochemical quantification and mean±standard error of the mean (SEM) for gene expression. Statistical significance was determined by student's t-test or one-way analysis of variance (ANOVA) followed by Tukey HSD test using SPSS 18.0 software (IBM, Armonk, N.Y.). Significance was determined at $P<0.05$.

Example 1

Figure 9:
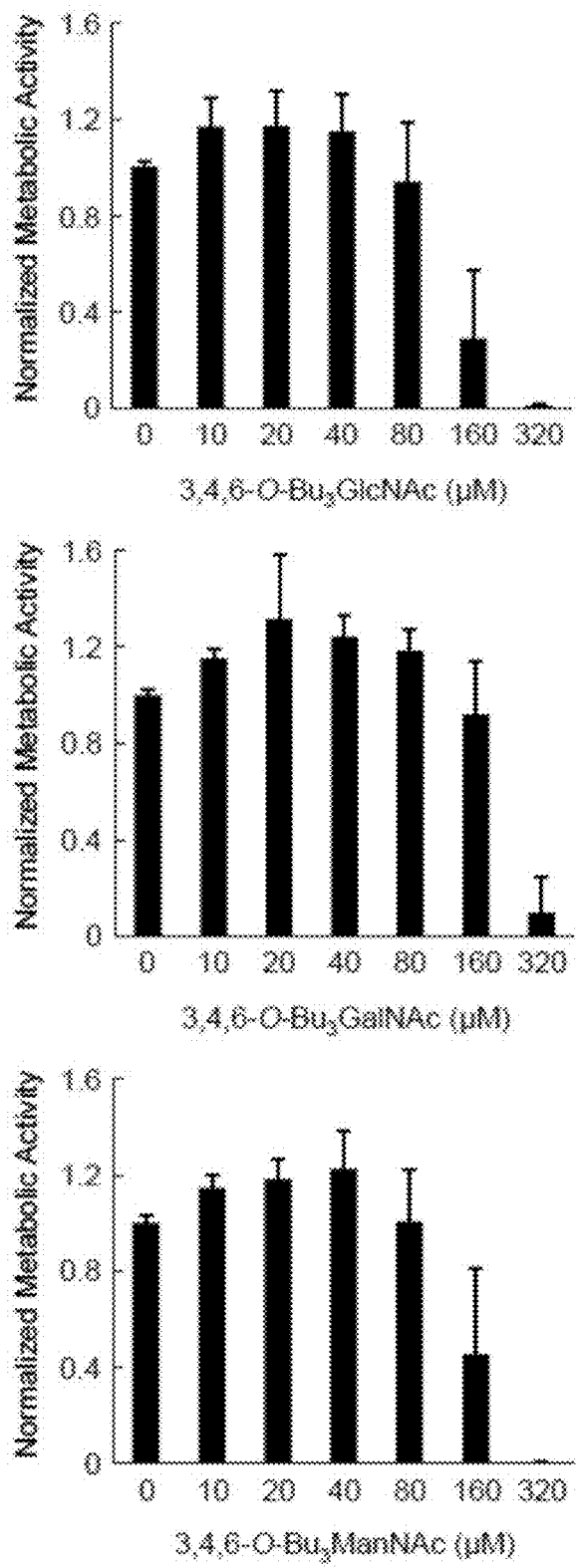
FIG. 9 shows WST-1 cell proliferation assay for the three analogs investigated.
Figure 10:
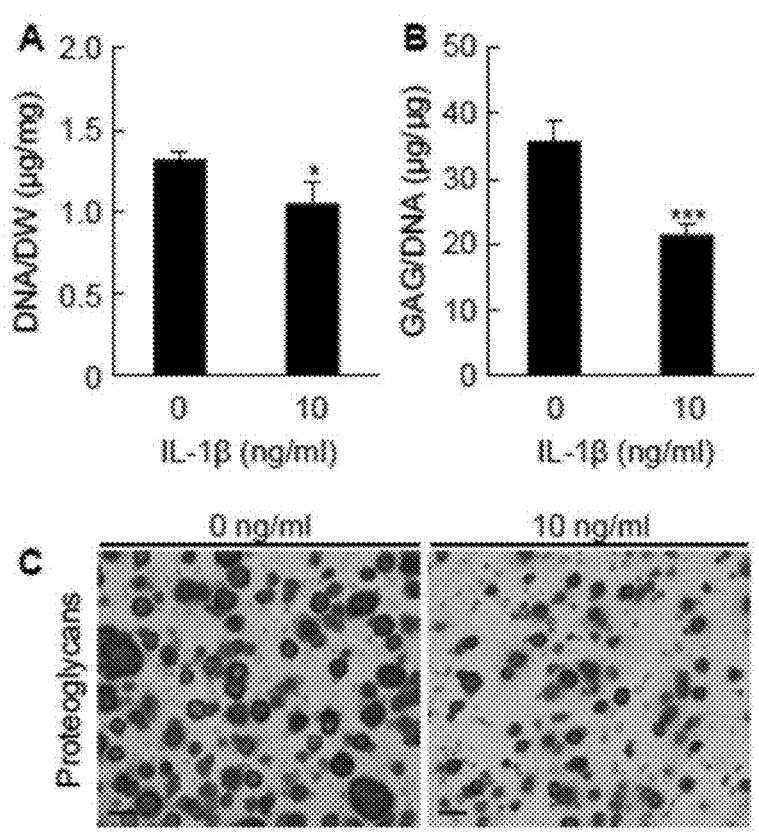
FIG. 10 depicts the effect of IL-1β stimulation on biochemical content of chondrogenic-induced MSCs encapsulated in PEGDA hydrogels. (A) DNA normalized to construct dry weight (n=3, *P<0.05) and (B) sGAG normalized to DNA content (n=3, ***P<0.001). (C) Histological staining for proteoglycans using Safranin-O (scale bar: 50 µm).

Effect of Tributanoylated Hexosamine Exposure on Monolayer Chondrocyte Viability. The chemical structures of 3,4,6-O-Bu$_3$GlcNAc, 3,4,6-O-Bu$_3$GalNAc, and 3,4,6-O-Bu$_3$ManNAc are shown in FIGS. 1A-C; these molecules are subsequently denoted as GlcNAc-a, GalNAc-a, and ManNAc-a in this application. Because of the previously reported toxicity of these compounds, the WST-1 assay was used to determine the dose-dependent viability of analog-treated chondrocytes so as to avoid cytotoxic levels. The analogs did not reduce cell viability at concentrations of less than 40 μM, while reduced viability was observed starting at concentrations of 80 μM for GlcNAc-a and ManNAc-a and 160 μM for GalNAc-a (FIG. 9). Based on these results, the subsequent studies were performed at analog concentrations of up to 150 μM.

Example 2

Figure 2:
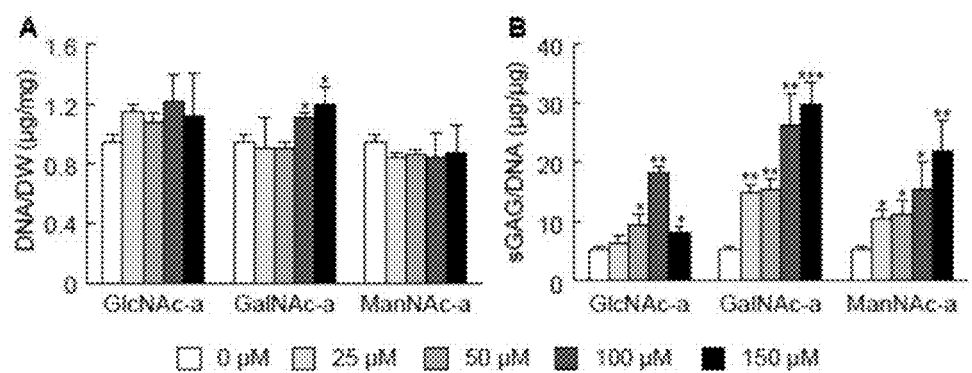
FIG. 2 shows biochemical analysis of DNA and sGAG for 3D hydrogels of bovine chondrocytes exposed to hexosamine analogs in combination with 10 ng/ml IL-1β. (A) Dry weight of DNA normalized to the construct had minimal variability across all conditions (n=3). (B) sGAG accumulation, normalized to DNA content, increased with increasing concentrations of hexosamine analog for all conditions except 150 µM GlcNAc-a exposure (n=3, * P<0.05, P<0.01, * P<0.001 versus no analog exposure).

Comparison of ECM Production by IL-1β-Stimulated Chondrocytes Exposed to Tributanoylated Hexosamine. After establishing the concentration range for maintaining cell viability with chondrocyte exposure to the three analogs in monolayer cell culture, we next sought to examine the effects of the hexosamine analogs on ECM accumulation by IL-1β-stimulated chondrocytes. As chondrocytes reside within a three-dimensional (3D) network in vivo, a 3D hydrogel culturing system was utilized for these studies (FIG. 1D). Also, 3D culture environments minimize chondrocyte dedifferentiation, commonly observed in monolayer cultures. Furthermore, PEGDA hydrogels serve as a "blank slate" with minimal cell and protein interactions to evaluate soluble signals. To model a disease state chondrocytes were exposed to the inflammatory cytokine, IL-1β, for the entire time course of the study. To determine the effect of hexosamine analogs on cell viability after 21 days of exposure within the 3D hydrogels, quantification of the DNA content was performed. DNA quantities were similar across all experimental groups (FIG. 2A).

Figure 3:
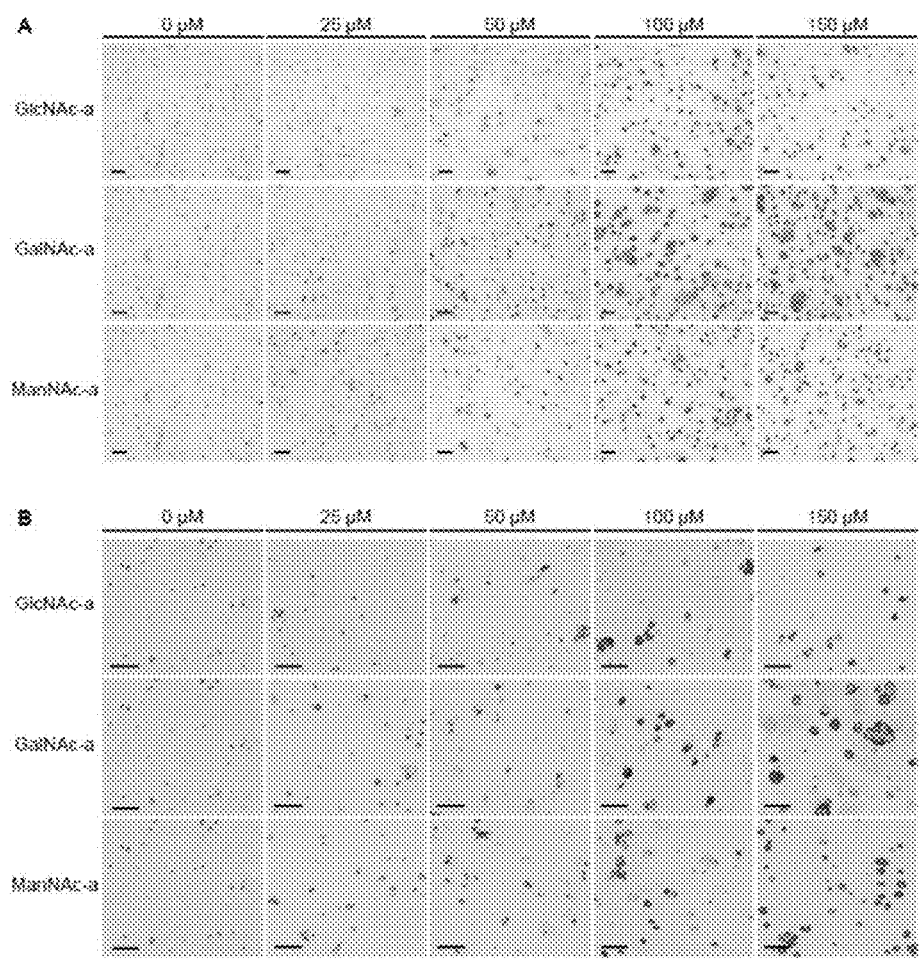
FIG. 3 is a histological analysis of IL-1β-stimulated chondrocytes exposed to hexosamine analogs in 3D hydrogels. (A) Safranin-O staining for proteoglycans and (B) type II collagen immunostaining (scale bar: 50 µm).

Cytokine stimulation decreases ECM accumulation by chondrocytes in a manner analogous to cartilage degeneration. Therefore, sGAG accumulation, a predominant ECM molecule in cartilage, was quantified within the cell-laden hydrogels using the DMMB dye assay and normalized to the DNA content of these hydrogels to account for variations in cell number between samples. Exposure of the hydrogels containing cytokine-stimulated chondrocytes to the analogs increased sGAG production. Specifically, all of the analogs increased sGAG accumulation in a dose-dependent manner up to 100 μM, with a further increase at 150 μM for GalNAc-a and ManNAc. However, in the case of GlcNAc-a treated chondrocytes, sGAG levels decreased at 150 μM compared to 100 μM (FIG. 2B), likely due to reduced metabolic activity accompanying slower proliferation of the cells (FIG. 9). The impact of the hexosamine analogs on sGAG production was confirmed via histological staining for proteoglycans using Safranin-O (FIG. 3A). An increase in proteoglycan deposition can be observed through 100 μM exposure for all analogs, with a further increase at 150 μM for GalNAc-a and ManNAc-a, as evident by red staining intensity when compared to untreated chondrocytes. To further characterize ECM production, type II collagen deposition in the hydrogels was visualized through use of immunohistochemistry. Analog exposure increased type II collagen deposition, indicated by the red/brown stain, starting at 50 μM for all analogs (FIG. 3B) with GalNAc-a exposure resulting in the highest staining intensity. These findings indicate that all three hexosamine analogs have positive effects on stimulating ECM accumulation by IL-1β-stimulated chondrocytes. Furthermore, GalNAc-a exposure induced the greatest cartilage-like tissue formation by the diseased cells, as indicated by increased levels of sGAG content, and proteoglycan and type II collagen staining intensity.

Example 3

Altered Gene Expression of IL-1β-Stimulated Chondrocytes Upon Hexosamine Analog Exposure. Interleukin-1β stimulation of chondrocytes decreases the gene expression levels of ECM proteins. Therefore, we sought to evaluate the gene expression changes of three ECM protein molecules—aggrecan, type II collagen and type I collagen—when chondrocytes were exposed to IL-1β and the hexosamine analogs. Chondrocytes increased gene expression of all three ECM molecules when exposed to each of the hexosamine analogs (FIGS. 4 A-C), consistent with the increased ECM accumulation observed (see FIG. 2B and FIG. 3).

Figure 4:
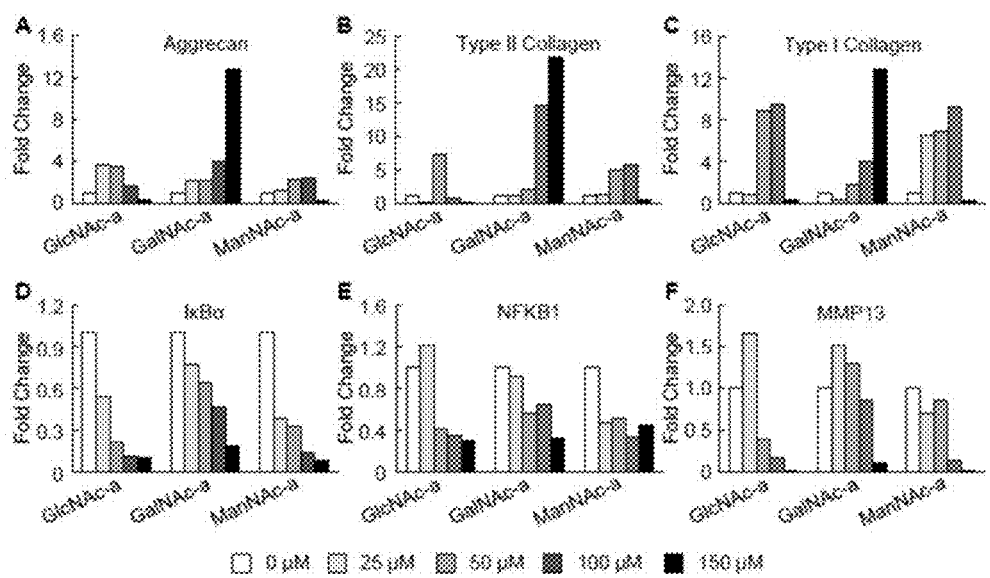
FIG. 4 depicts the effects of analog exposure on gene expression of IL-1β-stimulated chondrocytes in 3D hydrogels. Gene expression for ECM proteins (A) aggrecan, (B) type II collagen and (C) type I collagen, and inflammatory proteins (D) IκBα, (E) NFKB1 and (F) MMP13.

We further characterized the effects of exposing chondrocytes to the analog library by evaluating gene expression of transcriptional targets of NFκB, namely IκBα, NFKB1 and MMP13. All three hexosamine analogs reduced expression of NFKB1 along with a dose-dependent decrease in IκBα expression (FIGS. 4 D,E). Gene expression profiles for MMP13 demonstrated an initial maintenance or increase in expression at low concentrations of exposure, while at higher concentrations, all analogs decreased MMP13 gene expression (FIG. 4F). The MMP13 gene expression response, along with the decrease in IκBα and NFKB1 gene expression provide evidence that all three analogs act via a similar mechanism to alter the cellular behavior in the presence of IL-1β, namely, by reducing NFκB activity.

Example 4

Altered ECM Accumulation by Exposure of Chondrogenic Differentiating Mesenchymal Stem Cells to GalNAc-a. Mesenchymal stem cells are an important cell source for cartilage tissue repair after osteochondral trauma, microfracture surgery and in cell-based therapies. Therefore, we sought to evaluate the effects of GalNAc-a on the chondrogenic differentiation of MSCs. As in the chondrocyte experiments, cells were cultured in 3D hydrogels to better mimic the in vivo environment and support chondrogenesis (FIG. 1E). GalNAc-a was utilized for these studies because it facilitated the greatest recovery from IL-1β-induced matrix loss in chondrocytes. Additionally, dexamethasone, known to inhibit NFκB activity, was used as a control for these experiments. Dexamethasone is also a standard medium supplement for chondrogenic induction of MSCs, as it is thought to be necessary for stem cell differentiation. Finally, we chose to evaluate chondrogenesis in the presence or absence of ascorbic acid, which is required for collagen synthesis and is also an antioxidant that reduces inflammation through radical scavenging.

Figure 5:
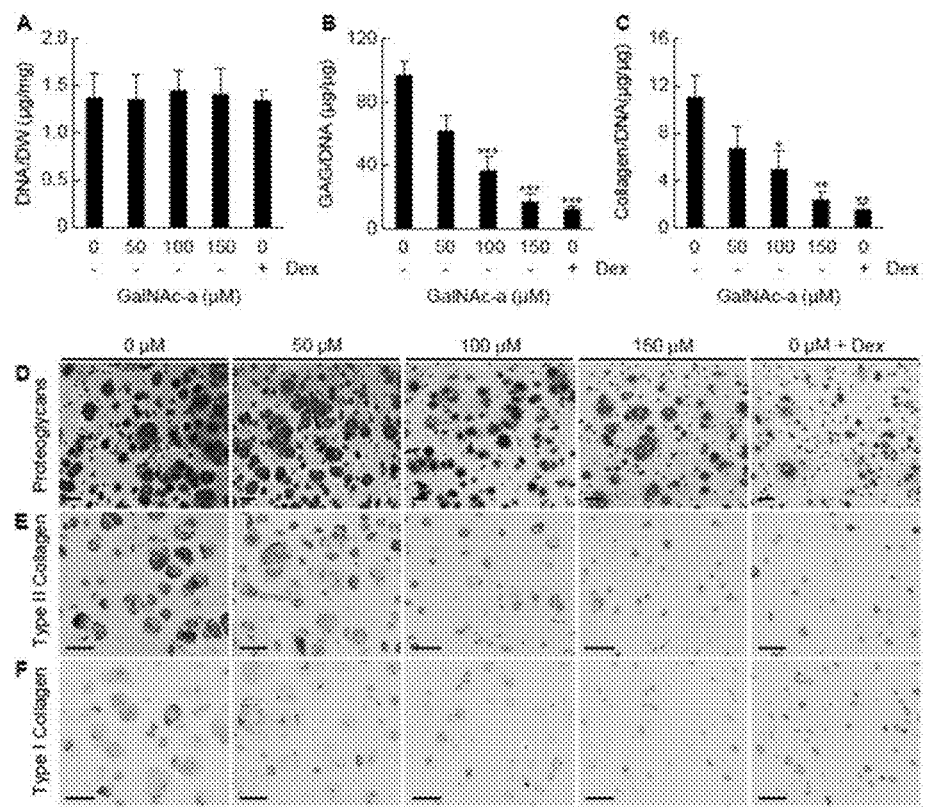
FIG. 5 is a biochemical analysis of MSCs undergoing chondrogenesis in the presence of ascorbic acid and GalNAc-a or dexamethasone in 3D hydrogels. Quantification of biochemical composition of (A) DNA normalized to construct dry weight, (B) sGAG normalized to DNA content and (C) total collagen normalized to DNA content (n=4, * P<0.05, ** P<0.01, * P<0.001 versus no analog exposure). (D) Histological staining for proteoglycans using Safranin-O and (E,F) immunohistochemical staining for (E) type II collagen and (F) type I collagen (scale bar: 50 µm).

To determine the impact of GalNAc-a exposure on ECM accumulation by chondrogenic-induced MSCs, we evaluated the biochemical content of the cell-laden hydrogels. GalNAc-a exposure did not change the DNA content in any of the groups evaluated (FIG. 5A and FIG. 7A). ECM accumulation was assessed via sGAG and total collagen quantification. Total collagen accumulation was assayed only in the ascorbic acid-containing medium samples because ascorbic acid is required for collagen synthesis and secretion from cells. GalNAc-a exposure produced a dose-dependent decrease in sGAG in both medium conditions assessed (FIG. 5B and FIG. 7B). Furthermore, GalNAc-a exposure induced a dose-dependent decrease in total collagen accumulation (FIG. 5C). Dexamethasone exposure resulted in a similar response as GalNAc-a exposure by reducing sGAG accumulation under both medium conditions (FIG. 5B and FIG. 7B). Dexamethasone exposure also reduced total collagen accumulation under ascorbic acid-containing chondrogenic induction conditions (FIG. 5C). The reduction in ECM accumulation was further confirmed via Safranin-O staining for proteoglycans (FIG. 5D and FIG. 7C), and immunohistochemistry for type II and type I collagen (FIGS. 5 E,F). These findings indicate that decreasing NFκB activity with GalNAc-a inhibits chondrogenic differentiation of the MSCs.

Example 5

Figure 6:
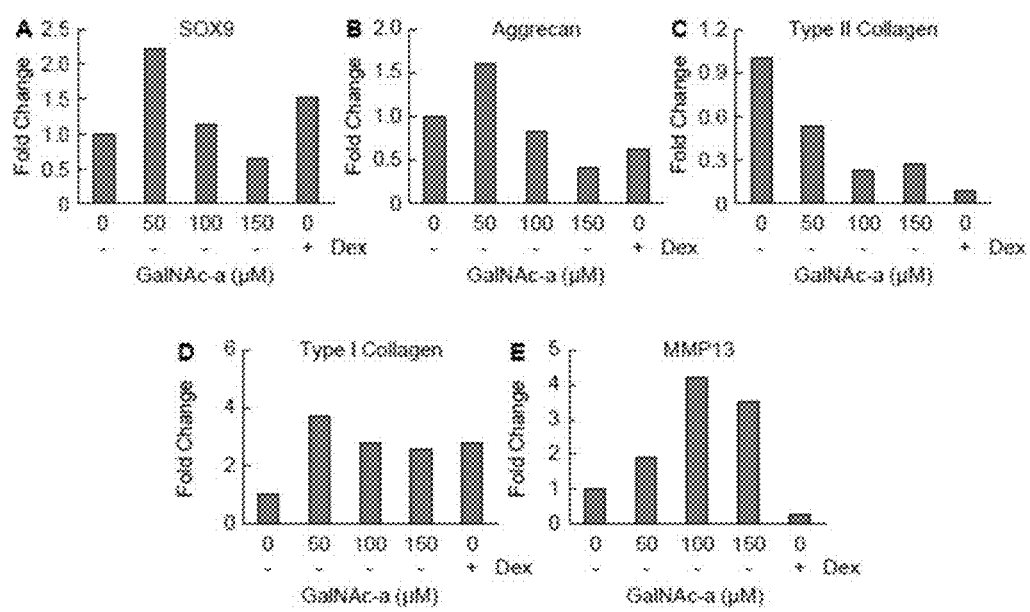
FIG. 6 shows gene expression analysis of MSCs undergoing chondrogenesis in the presence of ascorbic acid and GalNAc-a or dexamethasone in 3D hydrogels. Markers for (A-D) chondrogenesis and matrix production and (E) MMP13 were evaluated. All data were normalized to individual β-actin levels and presented relative to untreated controls (no analog, no dexamethasone).
Figure 7:
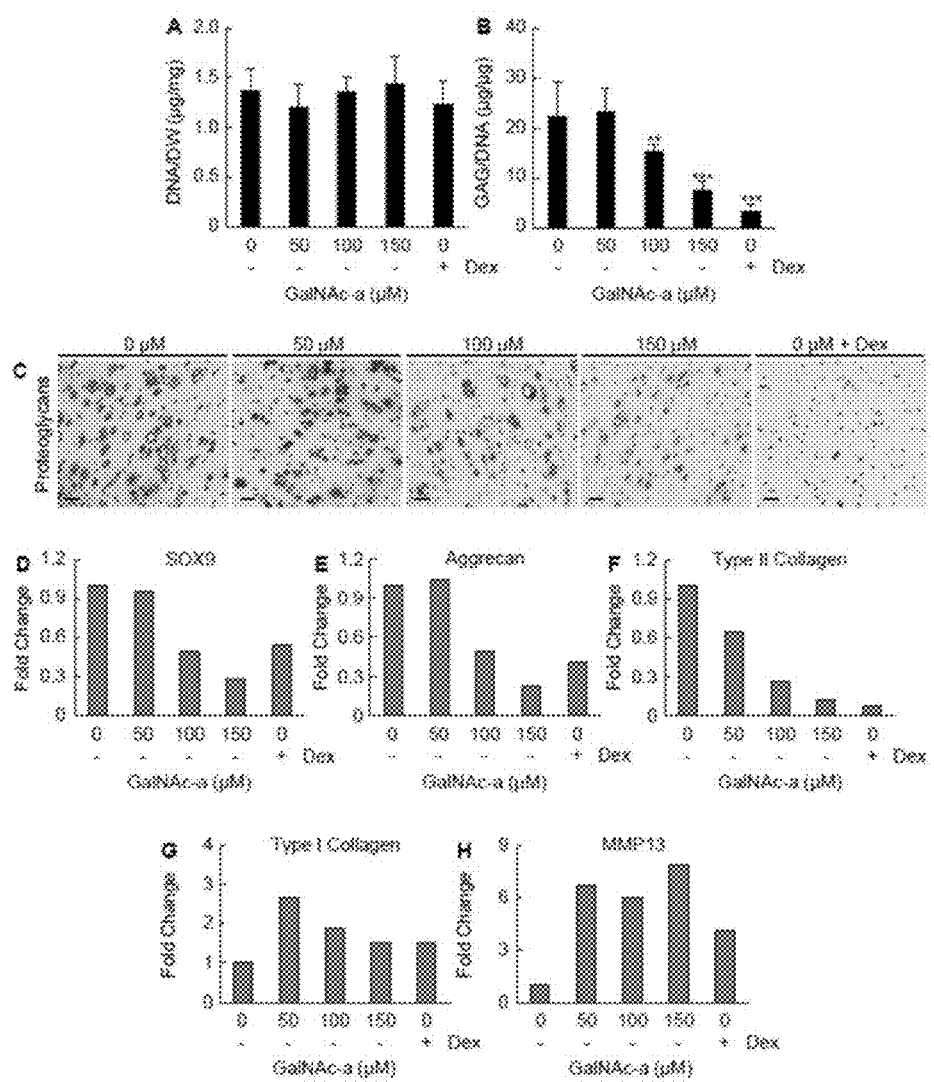
FIG. 7 shows biochemical and gene expression analysis of MSCs undergoing chondrogenesis (absence of ascorbic acid) in the presence of GalNAc-a or dexamethasone in 3D hydrogels. Quantification of biochemical composition of (A) DNA normalized to construct dry weight and (B) sGAG normalized to DNA content (n=4, P<0.01, * P<0.001 versus no analog exposure). (C) Histological staining for proteoglycans using Safranin-O (scale bar: 50 µm). Gene expression analysis of markers for (D-G) chondrogenesis and matrix production with (H) MMP13 were evaluated (presented as described in Figure Legend 6).

GalNAc-a Alters Gene Expression of Chondrogenic-Induced Mesenchymal Stem Cells. We next evaluated gene expression changes related to the chondrogenic markers SOX9, aggrecan and type II collagen, along with type I collagen, a marker for ubiquitous ECM production and fibrocartilage. The chondrogenic transcription factor, SOX9, decreased in a dose-dependent manner with 50 µM to 150 µM GalNAc-a exposure under both medium conditions (FIG. 6A and FIG. 7D). Fifty micromolar GalNAc-a exposure increased SOX9 expression in the ascorbic acid-containing medium group (FIG. 6A). Aggrecan expression followed a similar trend as SOX9 expression under both medium conditions (FIG. 6B and FIG. 7E). Additionally, GalNAc-a exposure decreased type II collagen expression under both medium conditions similar to the immunohistochemistry results (FIG. 6C and FIG. 7F). Type I collagen expression initially increased with 50 µM analog exposure and slightly decreased thereafter under both medium conditions, but remained elevated as compared to no analog exposure (FIG. 6D and FIG. 7G). Dexamethasone exposure decreased the expression of the ECM markers, aggrecan and type II collagen, while increasing expression of type I collagen, similar to the effects of analog exposure (FIG. 6 B-D and FIG. 7 E-G). Finally, we evaluated gene expression changes for MMP13 after GalNAc-a exposure of chondrogenic-induced MSCs. MMP13 expression increased at all analog concentrations under investigation, regardless of medium condition (FIG. 6E and FIG. 7H).

Example 6

Figure 8:
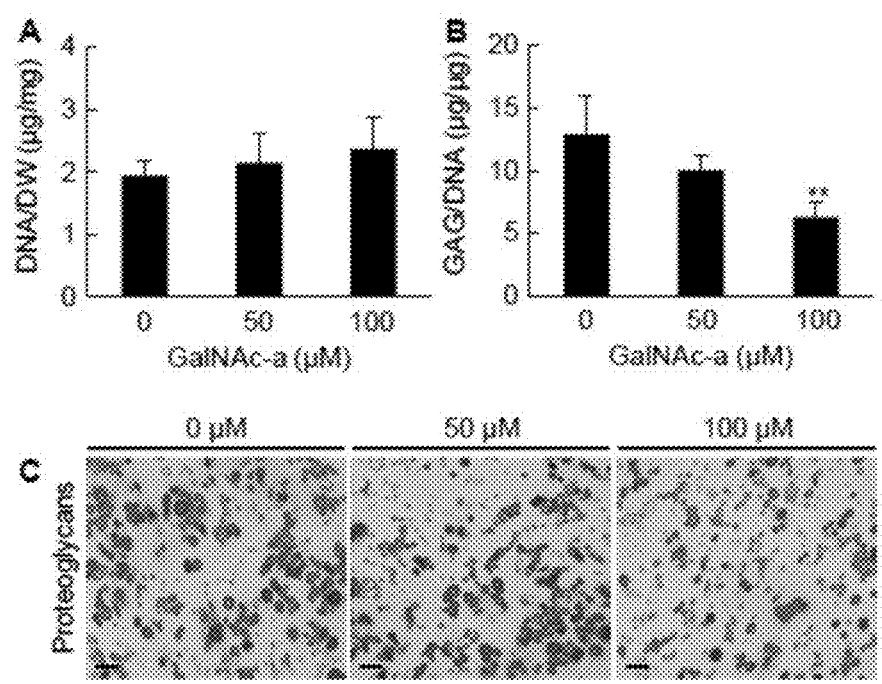
FIG. 8 depicts the biochemical analysis of MSCs undergoing chondrogenesis under IL-1β stimulation and GalNAc-a exposure in 3D hydrogels. (A) DNA normalized to construct dry weight and (B) sGAG normalized to DNA content (n=3, **P<0.01 versus no analog exposure). (C) Histological staining for proteoglycans using Safranin-O (scale bar: 50 µm).

GalNAc-a Alters ECM Accumulation of Chondrogenic-Induced Mesenchymal Stem Cells Stimulated by IL-1β. GalNAc-a exposure on chondrogenesis in the presence of IL-1β. IL-1β stimulation of chondrogenic-induced MSCs decreased both DNA content and sGAG accumulation (FIG. 17) similar to IL-1β effects alone on chondrocytes. GalNAc-a exposure of IL-1β stimulated chondrogenic-induced MSCs did not have an effect on DNA content (FIG. 8A). However, GalNAc-a exposure decreased sGAG accumulation in chondrogenic-induced MSCs exposed to IL-1β (FIGS. 8 B and C), similar to the trends observed in unstimulated MSCs (see FIG. 5B).

Example 7

Figure 11:
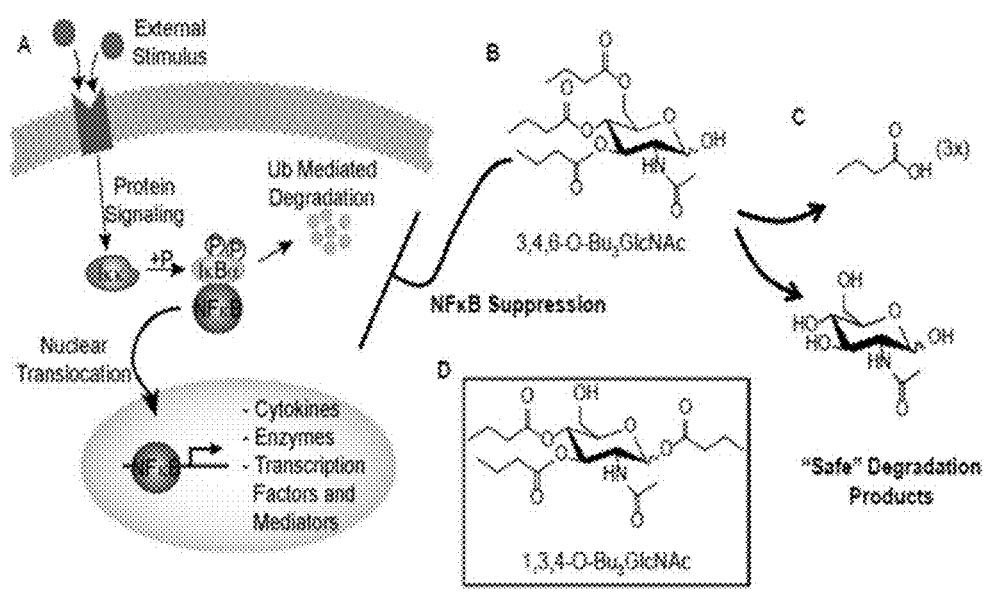
FIG. 11 depicts the impact of SCFA-hexosamine drug candidates on pathways connected to NFκB. (A) External stimuli results in an intracellular phosphorylation cascade activating NFκB signaling. (B) 3,4,6-O-Bu$_3$GlcNAc has a "whole molecule" structure-activity relationship (SAR) that decreases NFκB activity. (C) Degradation products of 3,4, 6-O-Bu$_3$GlcNAc are n-butyrate and GlcNAc, which are two natural metabolites that are safely and efficiently metabolized. (D) 1,3,4-O-Bu$_3$GlcNAc is the chemical isomer of 3,4,6-O-Bu$_3$GlcNAc which generates the same metabolites but has no effect on cells in these studies.
Figure 12:
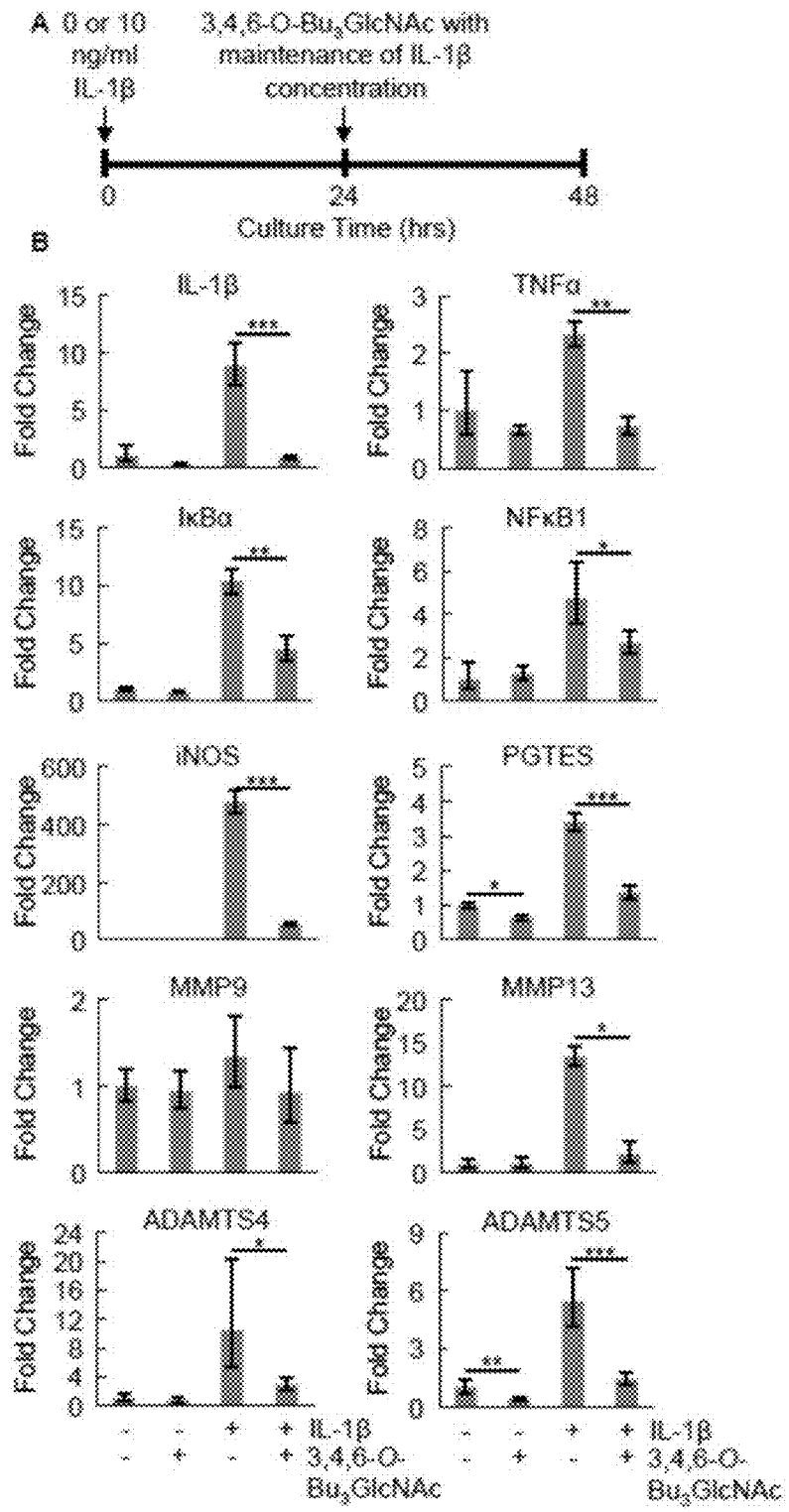
FIG. 12 shows the anti-inflammatory effects of 3,4,6-O-Bu$_3$GlcNAc exposure on chondrocytes in monolayer culture. (A) Timeline of monolayer gene expression study. (B) Expression levels of genes related to OA and NFκB signaling in the presence of 50 μM of 3,4,6-O-Bu$_3$GlcNAc with or without IL-1β. Data is presented as averages and SEM of 3 independent samples (* P<0.05,  P<0.01, *P<0.001 versus the negative control with respective IL-1β concentration).
Figure 17:
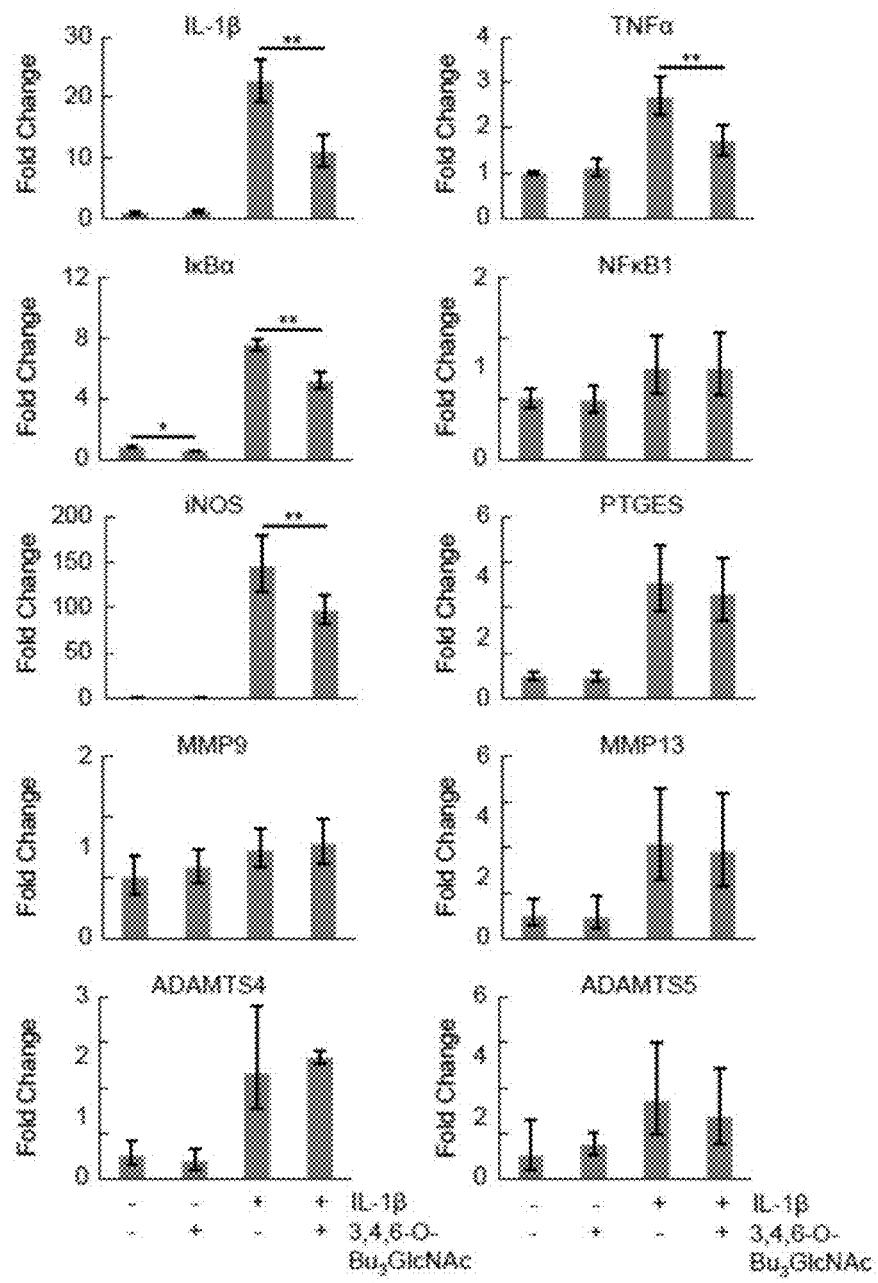
FIG. 17 shows the Effect of 50 μM 3,4,6-O-Bu$_3$GlcNAc exposure on chondrocytes cultured with or without IL-1β in monolayer after 4 hours of exposure (n=3, * P<0.05, ** P<0.01 versus the negative control with respective IL-1β concentration).

Early regulation of NFκB target genes by exposure of chondrocytes to 3,4,6-O-Bu$_3$GlcNAc. The biological impact of 3,4,6-O-Bu$_3$GlcNAc was initially evaluated in monolayer culture over 24 hours (FIG. 12). IL-1β stimulation was used to activate NFκB activity (FIG. 11A). Genes that are transcriptional targets of NFκB and are of relevance to OA were evaluated using real time PCR including IL-1β, MMP13, ADAMTS4, ADAMTS5, iNOS, PGES, and the transcription factor, NFκB1, and its inhibitor IκBα. All were upregulated after 48 hours of IL-1β exposure with the exception of MMP9. Exposure of the IL-1β stimulated chondrocytes to 3,4,6-O-Bu$_3$GlcNAc decreased the expression levels of all genes evaluated after 24 hours exposure again with the exception of MMP9 (FIG. 12). Additionally, 3,4,6-O-Bu$_3$GlcNAc in combination with IL-1β stimulation was able to alter expression levels of some of the genes after only 4 hours of exposure, specifically IL-1β, IκBα, and iNOS (FIG. 17).

Example 8

Figure 13:
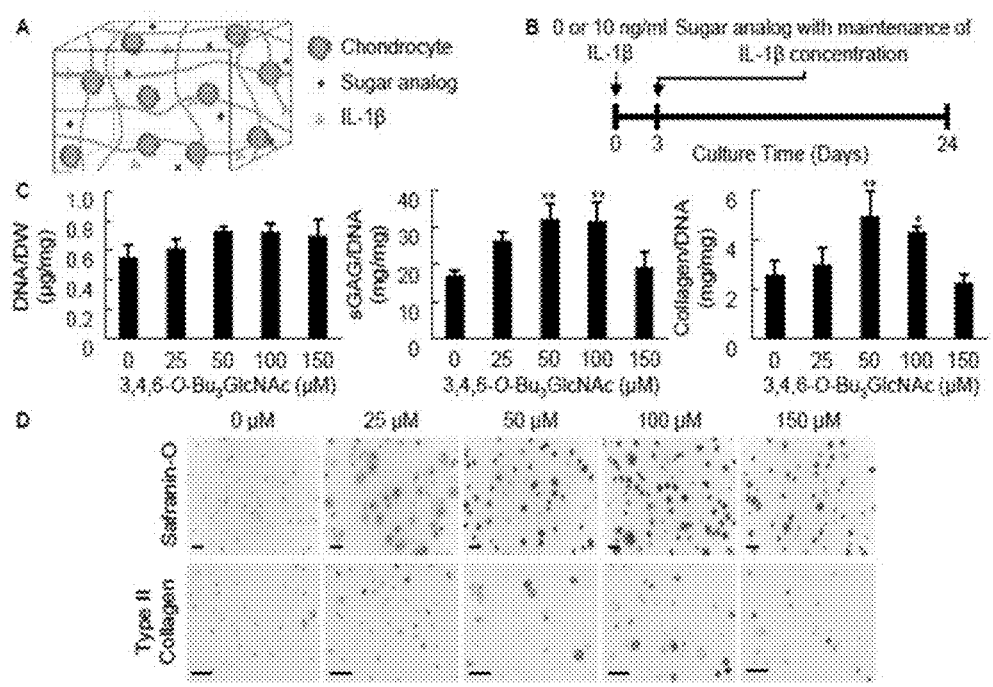
FIG. 13 depicts the effect of 3,4,6-O-Bu$_3$GlcNAc exposure on biochemical content of IL-1β stimulated chondrocytes in 3D hydrogels after 21 days of exposure. (A) Schematic of 3D culture system and (B) experimental time line (also applies to FIGS. 4-6). (C) DNA normalized to dry weight, sGAG normalized to DNA content and total collagen normalized to DNA content of the cell-laden hydrogels after 24 days of culture (n=3; * P<0.05, ** P<0.01 versus 0 μM 3,4,6-O-Bu$_3$GlcNAc exposure). (D) Histological staining for Safranin-O and immunostaining for type II collagen of the cell-laden hydrogels (scale bars: 50 μm) An increase in both stains can be observed at as low as 25 μM 3,4,6-O-Bu$_3$GlcNAc exposure but is more evident at 50 μM and 100 μM 25 μM 3,4,6-O-Bu$_3$GlcNAc exposure.
Figure 14:
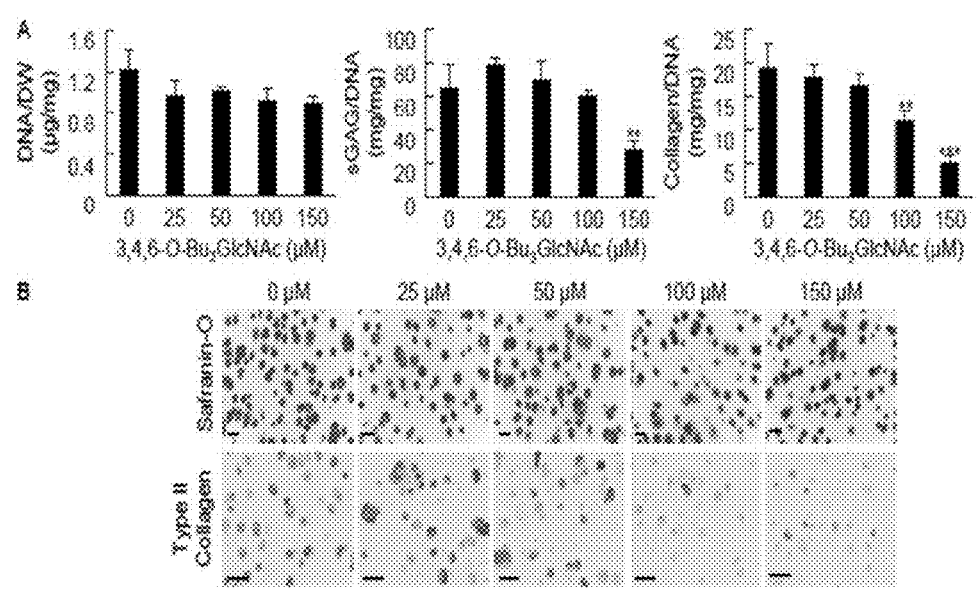
FIG. 14 shows the effect of 3,4,6-O-Bu$_3$GlcNAc exposure on biochemical content of unstimulated (no IL-1β exposure) chondrocytes in 3D hydrogel cultures. (A) DNA normalized to dry weight, sGAG normalized to DNA content and total collagen normalized to DNA content of the cell-laden hydrogels after 21 days of exposure (n=3,  P<0.01, * P<0.001). (B) Histological staining for safranin-O and immunostaining for type II collagen of the cell-laden hydrogels (scale bars: 50 μm).

3,4,6-O-Bu$_3$GlcNAc influence on ECM deposition by IL-1β stimulated chondrocytes. To elucidate the potential of 3,4,6-O-Bu$_3$GlcNAc to affect ECM accumulation, we evaluated the response of chondrocytes to this molecule when cultured in 3D with or without IL-1β. Chondrocytes were encapsulated in poly(ethylene glycol)-diacrylate (PEGDA) hydrogels to mimic a 3D tissue environment and help to maintain a chondrocytic phenotype as compared to monolayer cultures (FIGS. 13A and B). This hydrogel system has previously been shown to support chondrocyte viability and matrix production. The exposure of chondrocytes to 3,4,6-O-Bu$_3$GlcNAc did not elicit a statistically significant difference in cell viability, as evident by DNA content of the cell-laden hydrogels, after 21 days of exposure (FIG. 13C and FIG. 14A).

3,4,6-O-Bu$_3$GlcNAc stimulated sulfated glycosaminoglycan (sGAG) accumulation. Specifically, 3,4,6-O-Bu$_3$GlcNAc induced an increase in sGAG accumulation starting at 25 µM and continued through 100 µM 3,4,6-O-Bu$_3$GlcNAc exposure in IL-1β stimulated chondrocytes (FIG. 13C). This change in sGAG corresponded to an almost doubling in sGAG deposition with 50 µM 3,4,6-O-Bu$_3$GlcNAc exposure as compared to no 3,4,6-O-Bu$_3$GlcNAc exposure. However, the sGAG content decreased at 150 µM 3,4,6-O-Bu$_3$GlcNAc exposure to levels similar to no analog controls. The decrease is plausibly attributed to the onset of cell stress and toxicity, which was manifested more overtly in the form of reduced cell viability in monolayer culture. In unstimulated chondrocytes, 3,4,6-O-Bu$_3$GlcNAc did not have an effect on sGAG deposition until 150 µM 3,4,6-O-Bu$_3$GlcNAc exposure (FIG. 14A) where a decrease was observed. Histological staining for proteoglycans using Safranin-O morphologically confirmed the changes in sGAG accumulations (FIG. 13D and FIG. 14B).

To further investigate the impact of 3,4,6-O-Bu$_3$GlcNAc on ECM accumulation, total collagen content of the cell-laden hydrogels was quantified. 3,4,6-O-Bu$_3$GlcNAc induced a significant increase in total collagen accumulation at 50 µM and 100 µM 3,4,6-O-Bu$_3$GlcNAc exposure in IL-1β stimulated chondrocytes (FIG. 13C). This increase corresponded to an almost doubling in collagen accumulation compared to no 3,4,6-O-Bu$_3$GlcNAc exposure. Unstimulated chondrocytes maintained collagen accumulation through 50 µM 3,4,6-O-Bu$_3$GlcNAc exposure with a concentration dependent decrease thereafter (FIG. 14A). As total collagen deposition captures information on collagen content regardless of the type being produced we sought to determine the impact 3,4,6-O-Bu$_3$GlcNAc had on type II collagen, the most abundant type of collagen in articular cartilage, using immunohistochemistry. Similar to total collagen accumulation, 3,4,6-O-Bu$_3$GlcNAc induced an increase in type II collagen immunostaining at 50 µM and 100 µM 3,4,6-O-Bu$_3$GlcNAc exposure (FIG. 13D) in IL-1β stimulated chondrocytes. A slight increase in stain intensity was also observed at 25 µM and 150 µM 3,4,6-O-Bu$_3$GlcNAc exposure as compared to no analog exposure. Unstimulated chondrocytes exhibited no differences in type II collagen immunostaining through 50 µM 3,4,6-O-Bu$_3$GlcNAc exposure after which a dose-dependent decrease was observed thereafter (FIG. 14B).

Example 9

Figure 15:
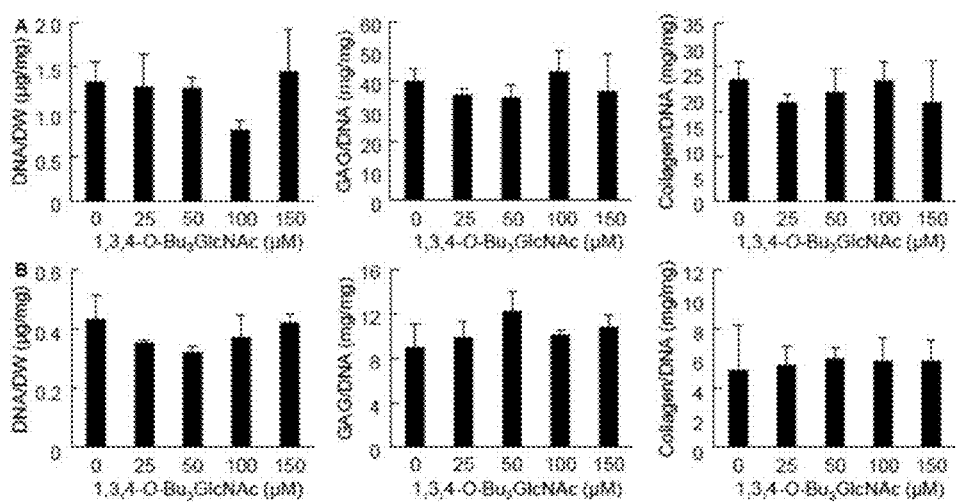
FIG. 15 depicts the effect of 1,3,4-O-Bu$_3$GlcNAc exposure on biochemical content on chondrocytes in 3D hydrogel cultures. (A) Chondrocytes without IL-1β stimulation exhibited no statistical differences in DNA normalized to dry weight, sGAG normalized to DNA content or total collagen normalized to DNA content. (B) IL-1β stimulated chondrocytes exhibited no statistical differences in DNA normalized to dry weight, sGAG normalized to DNA content or total collagen normalized to DNA content.

Unique chemical functionality required for ECM accumulation changes. After confirming the anti-inflammatory and chondroprotective potential of 3,4,6-O-Bu$_3$GlcNAc, we next sought to ensure that the observed results were not a result of the liberated GlcNAc or butyrate generated upon hydrolysis of the ester linkage in the analog (FIG. 11C). Therefore, we evaluated the ECM accumulation by chondrocytes exposed to 1,3,4-O-Bu$_3$GlcNAc, a molecule that has identical hydrolysis byproducts as 3,4,6-O-Bu$_3$GlcNAc. 1,3,4-O-Bu$_3$GlcNAc exposure produced no statistical differences in DNA content of the cell-laden hydrogels by unstimulated (FIG. 15A) or IL-1β stimulated chondrocytes (FIG. 15B). Additionally, 1,3,4-O-Bu$_3$GlcNAc did not alter the sGAG and total collagen deposition at the concentrations evaluated regardless of the inflammatory state (FIGS. 15 A and B). Therefore, while the previously mentioned contributions of the "core" GlcNAc to GAG production are expected to be occurring in our system based on literature precedent, the lack of activity of 1,3,4-O-Bu$_3$GlcNAc clearly demonstrate that metabolic flux considerations have a negligible impact on increased ECM deposition. Instead, the beneficial effects of 3,4,6-O-Bu$_3$GlcNAc emanate from the intact pharmacophore rather than from any latent effects of liberated hydrolysis products.

Example 10

Altered expression of ECM and inflammatory markers in response to 3,4,6-O-Bu$_3$GlcNAc exposure in 3D hydrogel cultures. We next evaluated the gene expression changes in chondrocytes exposed to 3,4,6-O-Bu$_3$GlcNAc for 21 days with and without IL-1β stimulation. 3,4,6-O-Bu$_3$GlcNAc exposure increased aggrecan and type II collagen gene expression at concentrations similar to the increased ECM accumulation in IL-1β stimulated chondryoctes (FIG. 16A). Additionally, 3,4,6-O-Bu$_3$GlcNAc exposure increased the expression of type I collagen at intermediate concentrations in IL-1β stimulated chondrocytes; whereas, a concentration-dependent decrease in expression was observed in unstimulated chondrocytes (FIG. 16A and FIG. 18A). The increases observed in IL-1β stimulated chondrocytes for aggrecan, type II collagen and type I collagen, though highly variable, approached expression levels found in unstimulated chondrocytes (FIG. 6A, grey bars compared to white bar).

Figure 16:
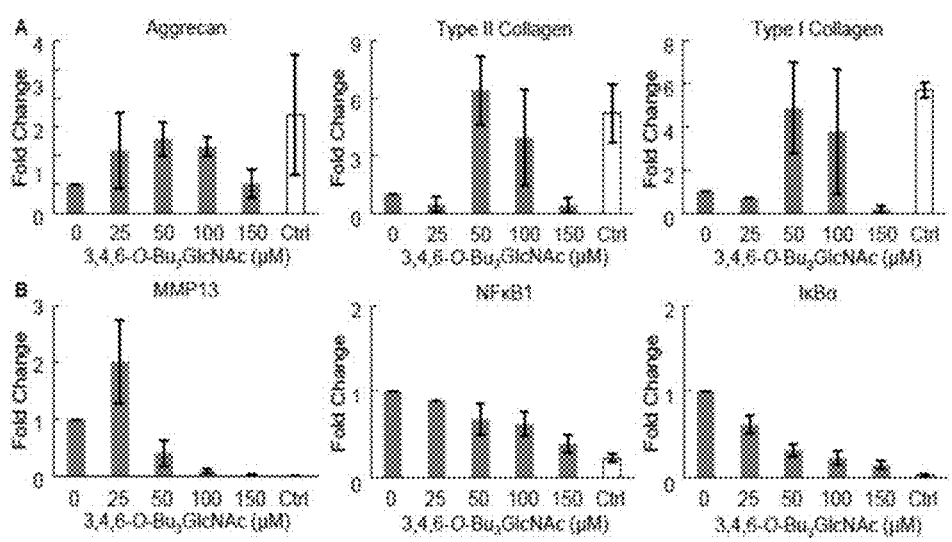
FIG. 16 shows the effect of 3,4,6-O-Bu$_3$GlcNAc exposure on gene expression of IL-1β stimulated chondrocytes in 3D hydrogel cultures after 21 days of exposure. (A) Gene expression for ECM markers, aggrecan, type II collagen and type I collagen. (B) Gene expression for inflammatory markers, MMP13, NFκB1 and IκBα (n=2 for 25 μM and 150 μM, n=3 for 0 μM, 50 μM and 100 μM. Ctrl denotes control chondrocytes without IL-1β stimulation. Data is presented as averages and SEM of RQ values).
Figure 18:
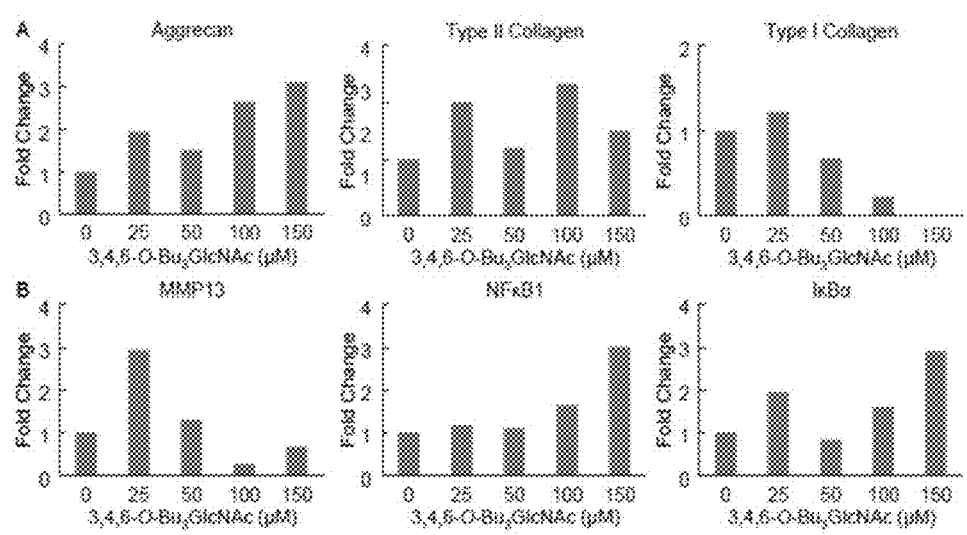
FIG. 18 depicts the Effect of 3,4,6-O-Bu$_3$GlcNAc exposure on gene expression of unstimulated chondrocytes in 3D hydrogel cultures. (A) Gene expression changes for ECM markers aggrecan, type II collagen and type I collagen. (B) Gene expression changes for inflammatory markers MMP13, NFκB1 and IκBα.

To evaluate the effect of 3,4,6-O-Bu$_3$GlcNAc on NFκB activity after 21 days of exposure, we investigated genes transcriptionally regulated by NFκB; specifically MMP13 for matrix degradation, and NFκB1 and IκBα for the auto-regulatory behavior of NFκB. An initial increase in MMP13 expression at the lowest dose of 3,4,6-O-Bu$_3$GlcNAc was observed followed by a decrease through 100 µM analog exposure regardless of inflammatory state (FIG. 16 B and FIG. 18 B). With IL-1β stimulated chondrocytes, a further decrease in MMP13 gene expression was observed at 150 µM 3,4,6-O-Bu$_3$GlcNAc exposure (FIG. 16 B). The initial increase in MMP13 gene expression observed may reflect ECM-mediated signaling as the cells begin to accumulate ECM. 3,4,6-O-Bu$_3$GlcNAc exposure decreased both IκBα and NFκB1 gene expression in IL-1β stimulated chondrocytes in a concentration-dependent manner (FIG. 16 B). Neither of these genes changed in unstimulated cells except at the highest concentrations studied, where an increase was observed likely due to toxic effects at high concentrations. Critical from the therapeutic perspective, exposure of the IL-1β stimulated chondrocytes to the analog decreased MMP13, NFκB1 and IκBα expression levels near to that of unstimulated (normal, healthy) chondrocytes (FIG. 16 B, grey bars compared to white bar).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I:

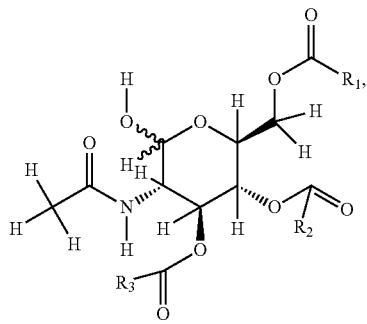

(I)

wherein $R_1$, $R_2$, and $R_3$ are the same or different, and are $C_2$-$C_3$ alkyl substituents; and a compound of formula II:

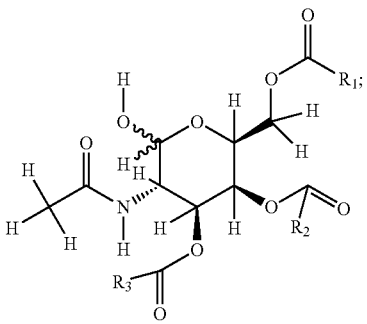

(II)

wherein $R_1$, $R_2$, and $R_3$ are the same or different, and are $C_2$-$C_6$ alkyl substituents.

2. The compound of claim 1, wherein $R_1$, $R_2$, and $R_3$ of the compounds of formulas I-II are $C_3$ alkyl groups and are selected from group consisting of:

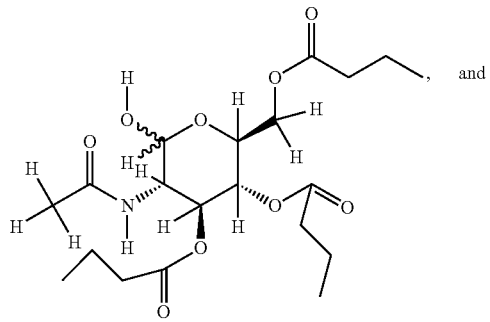

(compound 1)

and

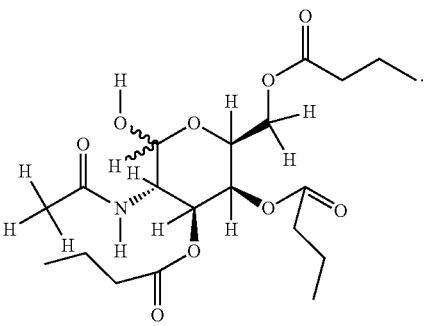

(compound 2)

3. A method for treating a joint disease in a subject comprising administering to the subject an effective amount of a compound of formula I:

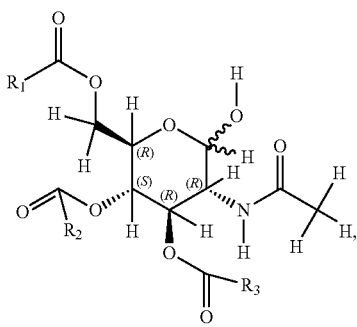

(I)

a compound of formula II:

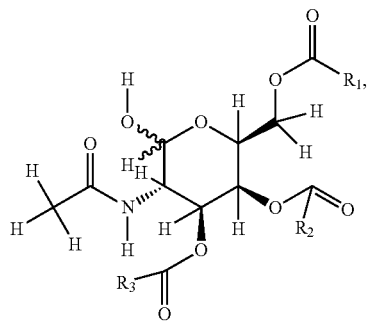

(II)

a compound of formula III:

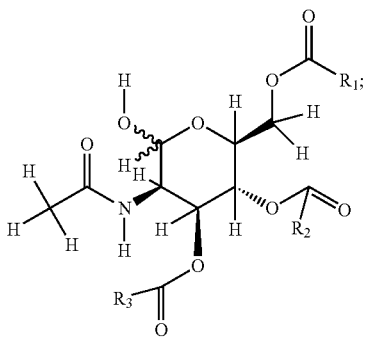

(III)

wherein $R_1$, $R_2$, and $R_3$ are the same or different, and are $C_1$-$C_6$ alkyl substituents.

4. The method of claim 3, wherein $R_1$, $R_2$, and $R_3$ of the compounds of formulas I-III are the same.

5. The method of claim 3, wherein $R_1$, $R_2$, and $R_3$ of the compounds of formulas I-III are $C_3$ alkyl groups and are selected from group consisting of:

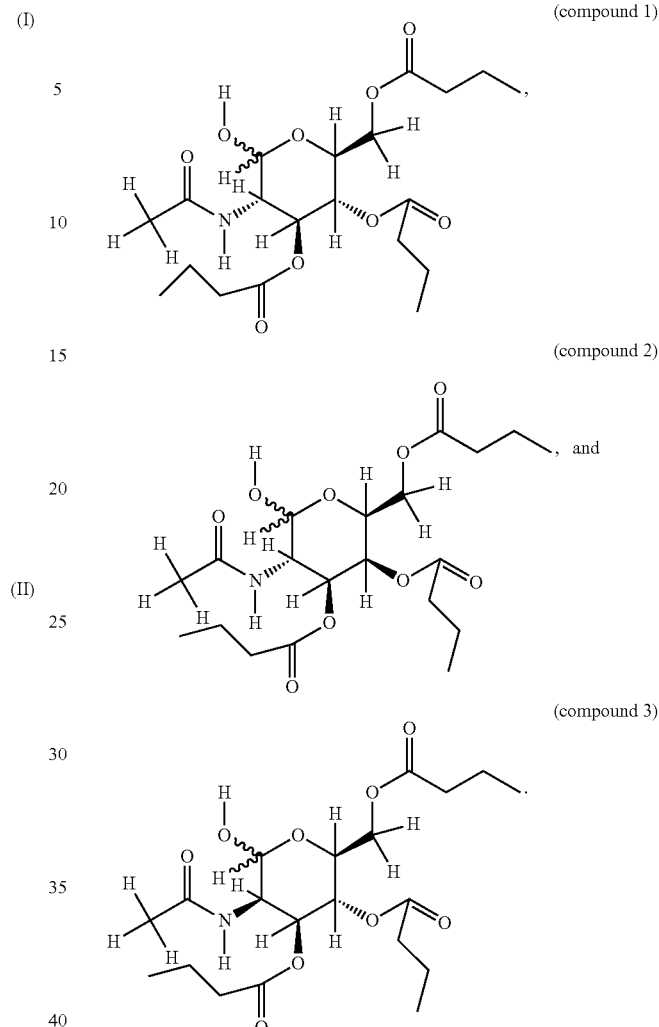

6. The method of claim 3, wherein the composition further comprises a biocompatible hydrogel.

7. The method of claim 6, wherein the biocompatible hydrogel is a cross-linked hydrophilic polymer matrix.

8. The method of claim 6, wherein the biocompatible polymer is in the form of hydrogels, fibers, nanofibers and sponges, and are selected from the group consisting of: Poly(ethylene glycol), Poly(propylene glycol), Poly(methyl vinyl ether), Oligoethylene, Poly(isobutylene) Poly(tetrahydrofuran) Poly(oxytrimethylene), Poly(dimethylsiloxsane), Poly(dimethylsilane), Nylon 6, Nylon 11, Poly(acrylonitrile), Squalane, Poly(1,3-dioxolane), Poly(iminooligomethylene), Poly(1-lysine), Polyethyleneimine, Poly(adipate), Poly(1-caprolactone), and Poly(L-lactic acid).

9. The method of claim 3, wherein the compounds are present in the composition and concentration of between about 1 μM to about 300 μM.

10. The method of claim 3, wherein the composition further comprises a second biologically active agent.

11. The method of claim 3, wherein the use increases extracellular matrix accumulation in chondrocytes stimulated by IL-1β.

12. The method of claim 3, wherein the use decreases NFKB1 gene expression in chondrocytes stimulated by IL-1β.

* * * * *

SEQUENCE LISTING

```
<160> NUMBER OF SEQ ID NOS: 40

<210> SEQ ID NO 1
<211> LENGTH: 19
<212> TYPE: DNA
<213> ORGANISM: Bos taurus

<400> SEQUENCE: 1
catcgggctt gccagagtt                                                       19

<210> SEQ ID NO 2
<211> LENGTH: 22
<212> TYPE: DNA
<213> ORGANISM: Bos taurus

<400> SEQUENCE: 2
actggtgtcc acgaacgtaa tg                                                   22

<210> SEQ ID NO 3
<211> LENGTH: 22
<212> TYPE: DNA
<213> ORGANISM: Bos taurus

<400> SEQUENCE: 3
gggcaacagc agattcactt ac                                                   22

<210> SEQ ID NO 4
<211> LENGTH: 20
<212> TYPE: DNA
<213> ORGANISM: Bos taurus

<400> SEQUENCE: 4
caaggatagg caggcgagat                                                      20

<210> SEQ ID NO 5
<211> LENGTH: 20
<212> TYPE: DNA
<213> ORGANISM: Bos taurus

<400> SEQUENCE: 5
gcaaccctgg aactgatgga                                                      20

<210> SEQ ID NO 6
<211> LENGTH: 20
<212> TYPE: DNA
<213> ORGANISM: Bos taurus

<400> SEQUENCE: 6
```
gctcacccgt ttgaccttttt          20

<210> SEQ ID NO 7
<211> LENGTH: 20
<212> TYPE: DNA
<213> ORGANISM: Bos taurus

<400> SEQUENCE: 7
gcaggccacc aactacaatg          20

<210> SEQ ID NO 8
<211> LENGTH: 20
<212> TYPE: DNA
<213> ORGANISM: Bos taurus

<400> SEQUENCE: 8
agtgacacca ggtcgggatt          20

<210> SEQ ID NO 9
<211> LENGTH: 20
<212> TYPE: DNA
<213> ORGANISM: Bos taurus

<400> SEQUENCE: 9
ttacaaaacc agcctccgtg          20

<210> SEQ ID NO 10
<211> LENGTH: 19
<212> TYPE: DNA
<213> ORGANISM: Bos taurus

<400> SEQUENCE: 10
gccgaaactg tccgagaaa          19

<210> SEQ ID NO 11
<211> LENGTH: 20
<212> TYPE: DNA
<213> ORGANISM: Bos taurus

<400> SEQUENCE: 11
tagcacgcac gacatctttc          20

<210> SEQ ID NO 12
<211> LENGTH: 20
<212> TYPE: DNA
<213> ORGANISM: Bos taurus

<400> SEQUENCE: 12
gaaggtcacg tagcccacat          20

<210> SEQ ID NO 13
<211> LENGTH: 18
<212> TYPE: DNA
<213> ORGANISM: Bos taurus

<400> SEQUENCE: 13
gctcacgctt tccctcct          18

<210> SEQ ID NO 14
<211> LENGTH: 20
<212> TYPE: DNA
<213> ORGANISM: Bos taurus

<400> SEQUENCE: 14

-continued

| | |
|---|---|
| caaactcatg ggcagcaaca | 20 |

<210> SEQ ID NO 15
<211> LENGTH: 20
<212> TYPE: DNA
<213> ORGANISM: Bos taurus

<400> SEQUENCE: 15

| | |
|---|---|
| tcgaagccgg gacagggagg | 20 |

<210> SEQ ID NO 16
<211> LENGTH: 20
<212> TYPE: DNA
<213> ORGANISM: Bos taurus

<400> SEQUENCE: 16

| | |
|---|---|
| cctcccggga tgcgagtcca | 20 |

<210> SEQ ID NO 17
<211> LENGTH: 22
<212> TYPE: DNA
<213> ORGANISM: Bos taurus

<400> SEQUENCE: 17

| | |
|---|---|
| tcactgccta cttagccctg aa | 22 |

<210> SEQ ID NO 18
<211> LENGTH: 21
<212> TYPE: DNA
<213> ORGANISM: Bos taurus

<400> SEQUENCE: 18

| | |
|---|---|
| gctccaaccg ctgtagttca t | 21 |

<210> SEQ ID NO 19
<211> LENGTH: 21
<212> TYPE: DNA
<213> ORGANISM: Bos taurus

<400> SEQUENCE: 19

| | |
|---|---|
| cgtcttcctg ggacattttc g | 21 |

<210> SEQ ID NO 20
<211> LENGTH: 20
<212> TYPE: DNA
<213> ORGANISM: Bos taurus

<400> SEQUENCE: 20

| | |
|---|---|
| tgccagtcct cggggttatt | 20 |

<210> SEQ ID NO 21
<211> LENGTH: 20
<212> TYPE: DNA
<213> ORGANISM: Bos taurus

<400> SEQUENCE: 21

| | |
|---|---|
| acaccatgag caccaaaagc | 20 |

<210> SEQ ID NO 22
<211> LENGTH: 20
<212> TYPE: DNA
<213> ORGANISM: Bos taurus

-continued

```
<400> SEQUENCE: 22
gcaaccagga ggaaggagaa                                              20

<210> SEQ ID NO 23
<211> LENGTH: 20
<212> TYPE: DNA
<213> ORGANISM: Bos taurus

<400> SEQUENCE: 23
ccgctcccgt ccttgcatcc                                              20

<210> SEQ ID NO 24
<211> LENGTH: 20
<212> TYPE: DNA
<213> ORGANISM: Bos taurus

<400> SEQUENCE: 24
ccgccctgga gcctttgtg                                               20

<210> SEQ ID NO 25
<211> LENGTH: 21
<212> TYPE: DNA
<213> ORGANISM: Bos taurus

<400> SEQUENCE: 25
tgcctcagag cccaccggaa t                                            21

<210> SEQ ID NO 26
<211> LENGTH: 20
<212> TYPE: DNA
<213> ORGANISM: Bos taurus

<400> SEQUENCE: 26
agtgcatccg ggcgacgaag                                              20

<210> SEQ ID NO 27
<211> LENGTH: 25
<212> TYPE: DNA
<213> ORGANISM: Bos taurus

<400> SEQUENCE: 27
tggcaccaca ccttctacaa tgagc                                        25

<210> SEQ ID NO 28
<211> LENGTH: 25
<212> TYPE: DNA
<213> ORGANISM: Bos taurus

<400> SEQUENCE: 28
gcacagcttc tccttaatgt cacgc                                        25

<210> SEQ ID NO 29
<211> LENGTH: 21
<212> TYPE: DNA
<213> ORGANISM: Capra aegagrus

<400> SEQUENCE: 29
cacgatgcct ttcaccacga c                                            21

<210> SEQ ID NO 30
<211> LENGTH: 21
<212> TYPE: DNA
<213> ORGANISM: Capra aegagrus
```

```
<400> SEQUENCE: 30
tgcgggtcaa cagtgcctat c                                              21

<210> SEQ ID NO 31
<211> LENGTH: 20
<212> TYPE: DNA
<213> ORGANISM: Capra aegagrus

<400> SEQUENCE: 31
agggccaaga cgaagacatc                                                20

<210> SEQ ID NO 32
<211> LENGTH: 21
<212> TYPE: DNA
<213> ORGANISM: Capra aegagrus

<400> SEQUENCE: 32
agatcacgtc atcgcacaac a                                              21

<210> SEQ ID NO 33
<211> LENGTH: 21
<212> TYPE: DNA
<213> ORGANISM: Capra aegagrus

<400> SEQUENCE: 33
gtggagcagc aagagcaagg a                                              21

<210> SEQ ID NO 34
<211> LENGTH: 21
<212> TYPE: DNA
<213> ORGANISM: Capra aegagrus

<400> SEQUENCE: 34
cttgccccac ttaccagtgt g                                              21

<210> SEQ ID NO 35
<211> LENGTH: 20
<212> TYPE: DNA
<213> ORGANISM: Capra aegagrus

<400> SEQUENCE: 35
ttcatgaaga tgaccgacga                                                20

<210> SEQ ID NO 36
<211> LENGTH: 20
<212> TYPE: DNA
<213> ORGANISM: Capra aegagrus

<400> SEQUENCE: 36
cacaccatga aggcgttcat                                                20

<210> SEQ ID NO 37
<211> LENGTH: 18
<212> TYPE: DNA
<213> ORGANISM: Capra aegagrus

<400> SEQUENCE: 37
gctcacgctt tccctcct                                                  18

<210> SEQ ID NO 38
<211> LENGTH: 20
<212> TYPE: DNA
```

```
<213> ORGANISM: Capra aegagrus

<400> SEQUENCE: 38
caaactcatg ggcagcaaca                                              20

<210> SEQ ID NO 39
<211> LENGTH: 25
<212> TYPE: DNA
<213> ORGANISM: Capra aegagrus

<400> SEQUENCE: 39
tggcaccaca ccttctacaa tgagc                                        25

<210> SEQ ID NO 40
<211> LENGTH: 25
<212> TYPE: DNA
<213> ORGANISM: Capra aegagrus

<400> SEQUENCE: 40
gcacagcttc tccttaatgt cacgc                                        25
```